US010036067B2

(12) United States Patent
Raskind et al.

(10) Patent No.: US 10,036,067 B2
(45) Date of Patent: Jul. 31, 2018

(54) ISOLATED NUCLEIC ACIDS AND KITS FOR IDENTIFYING SUBJECTS SUSCEPTIBLE TO ATAXIC NEUROLOGICAL DISEASE

(75) Inventors: Wendy H. Raskind, Seattle, WA (US); Dong-Hui Chen, Seattle, WA (US); Thomas D. Bird, Lake Forest Park, WA (US); Zoran Brkanac, Seattle, WA (US)

(73) Assignee: University of Washington, Seattle, WA (US)

( * ) Notice: Subject to any disclaimer, the term of this patent is extended or adjusted under 35 U.S.C. 154(b) by 630 days.

(21) Appl. No.: 12/631,722

(22) Filed: Dec. 4, 2009

(65) Prior Publication Data

US 2010/0129823 A1 May 27, 2010

Related U.S. Application Data

(62) Division of application No. 10/671,007, filed on Sep. 25, 2003, now Pat. No. 7,655,401.

(60) Provisional application No. 60/414,816, filed on Sep. 26, 2002.

(51) Int. Cl.
*C12Q 1/68* (2018.01)
*C07H 21/04* (2006.01)
*C12Q 1/6883* (2018.01)

(52) U.S. Cl.
CPC ..... *C12Q 1/6883* (2013.01); *C12Q 2600/156* (2013.01); *C12Q 2600/16* (2013.01)

(58) Field of Classification Search
None
See application file for complete search history.

(56) References Cited

FOREIGN PATENT DOCUMENTS

WO WO 9947706 A1 * 9/1999
WO WO 0053218 A1 * 9/2000

OTHER PUBLICATIONS

Ahern, H. The Scientist 9(15):20 (1995).*
Chen, D.H. et al. Neurology 64:1258-1260 (2005).*
Al-Maghtheh, M. et al. Am. J. Hum. Genet. 62:1248-1252 (1998).*
Yabe, I. et al. Arch. Neurol. 60:1749-1751 (Dec. 2003).*
"Moiety" definition, obtained from Biology-Online Dictionary on Sep. 22, 2017, www.biology-online.org/dictionary/Moiety; 1 page.*
Abeliovich, A., et al., "PKCγ Mutant Mice Exhibit Mild Deficits in Spatial and Contextual Learning," Cell 75(7):1263-1271, Dec. 1993.
Brkanac, Z., et al., "A New Dominant Spinocerebellar Ataxia Linked to Chromosome 19q13.4-qter," Archives of Neurology 59:1291-1295, Aug. 2002.
Brkanac, Z., et al., "Autosomal Dominant Sensory/Motor Neuropathy With Ataxia (SMNA): Linkage to Chromosome 7q22-q32," American Journal of Medical Genetics (Neuropsychiatric Genetics) 114(4):450-457, May 2002.
Burright, E.N., et al., "SCA1 Transgenic Mice: A Model for Neurodegeneration Caused by an Expanded CAG Trinucleotide Repeat," Cell 82(6):937-948, Sep. 1995.
Chen, C., et al., "Impaired Motor Coordination Correlates With Persistent Multiple Climbing Fiber Innervation in PKCγ Mutant Mice," Cell 83:1233-1242, Dec. 1995.
Chen, D.-H., et al., "Cerebral Cavernous Malformation: Novel Mutation in a Chinese Family and Evidence for Heterogeneity," J. Neurological Sciences 196(1-2):91-96, Apr. 2002.
Chen, D.-H., et al., "Missense Mutations in the Regulatory Domain of PKCγ: A New Mechanism for Dominant Nonepisodic Cerebellar Ataxia," Am. J. Hum. Genet. 72(4):839-849, Apr. 2003.
Clark, H.B., et al., "Purkinje Cell Expression of a Mutant Allele of SCA1 in Transgenic Mice Leads to Disparate Effects on Motor Behaviors, Followed by a Progressive Cerebellar Dysfunction and Histological Alterations," Journal of Neuroscience 17(19):7385-7395, Oct. 1997.
Coussens, L., et al., "Multiple, Distinct Forms of Bovine and Human Protein Kinase C Suggest Diversity in Cellular Signaling Pathways," Science 233(4766):859-866, Aug. 1986.
Kazanietz, M.G., et al., "Residues in the Second Cysteine-rich Region of Protein Kinase C δ Relevant to Phorbol Ester Binding as Revealed by Site-Directed Mutagenesis," Journal of Biological Chemistry 270(37):21852-21859, Sep. 1995.
Klement, I.A., et al., "Ataxin-1 Nuclear Localization and Aggregation: Role in Polyglutamine-Induced Disease in SCA1 Transgenic Mice," Cell 95:41-53, Oct. 2, 1998.
Knopf, J.L., et al., "Cloning and Expression of Multiple Protein Kinase C cDNAs," Cell 46(4):491-502, Aug. 1986.
Mariotti, C. and S. Di Donato, "Cerebellar/Spinocerebellar Syndromes," Neurological Sciences 22(Suppl 2):S88-S92, Nov. 2001.
Mosely, M.L., et al., "Incidence of Dominant Spinocerebellar and Friedreich Triplet Repeats Among 361 Ataxia Families," Neurology 51(6):1666-1671, Dec. 1998.
Newton, A.C., "Protein Kinase C: Structural and Spatial Regulation by Phosphorylation, Cofactors, and Macromolecular Interactions," Chemical Reviews 101(8):2353-2364, Aug. 2001.
Quest, A.F.G., et al., "A Phorbol Ester Binding Domain of Protein Kinase Cγ: Deletion Analysis of the CYS2 Domain Defines a Minimal 43-Amino Acid Peptide," Journal of Biological Chemistry 269(4):2961-2970, Jan. 1994.

(Continued)

*Primary Examiner* — Diana B Johannsen
(74) *Attorney, Agent, or Firm* — Christensen O'Connor Johnson Kindness PLLC

(57) ABSTRACT

In one aspect, the invention provides methods of identifying genetic mutations that are associated with ataxic neurological disease. The methods comprise identifying a difference between a nucleic acid sequence of a protein kinase C gamma gene from a mammalian subject exhibiting ataxia and a nucleic acid sequence of a protein kinase C gamma gene from a subject which is not exhibiting ataxia, wherein the difference is a genetic mutation associated with ataxic neurological disease. In another aspect, isolated nucleic acid molecules encoding protein kinase C gamma missense mutations are provided. In another aspect, a method of screening a subject to determine if the subject has a genetic predisposition to develop an ataxic neurological disease is provided. In another aspect, the invention provides kits for determining susceptibility or presence of ataxic neurological disease in a mammalian subject.

12 Claims, No Drawings

(56) References Cited

OTHER PUBLICATIONS

Raskind, W.H., et al., "Loss of Heterozygosity in Chondrosarcomas for Markers Linked to Hereditary Multiple Exostoses Loci on Chromosomes 8 and 11," American Journal of Human Genetics 56(5):1132-1139, May 1995.
Rosenberg, R.N., "Autosomal Dominant Cerebellar Phenotypes: The Genotype Has Settled the Issue," Neurology 45(1):1-5, Jan. 1995.
Saito, N., et al., "Distribution of Protein Kinase C-Like Immunoreactive Neurons in Rat Brain," Journal of Neuroscience 8(2):369-382, Feb. 1988.
Skinner, P.J., et al., "Altered Trafficking of Membrane Proteins in Purkinje Cells of SCA1 Transgenic Mice," American Journal of Pathology 159(3):905-913, Sep. 2001.
Tanaka, C., and Y. Nishizuka, "The Protein Kinase C Family for Neuronal Signaling," Annual Review of Neuroscience 17:551-567, 1994.
Van Swieten, J.C., et al., "A Mutation in the Fibroblast Growth Factor 14 Gene Is Associated With Autosomal Dominant Cerebral Ataxia," American Journal of Human Genetics 72(1):191-199, Jan. 2003.
Xu, R.X., et al., "NMR Structure of a Protein Kinase C-γ Phorbol-Binding Domain and Study of Protein-Lipid Micelle Interactions," Biochemistry 36(35):10709-10717, Sep. 1997.
Yamashita, I., et al., "A Novel Locus for Dominant Cerebellar Ataxia (SCA14) Maps to a 10.2-cM Interval Flanked by D19S206 and D19S605 on Chromosome 19q13.4-qter," Annals of Neurology 48(2):156-163, Aug. 2000.
Zhang, G., et al., "Crystal Structure of the Cys2 Activator-Binding Domain of Protein Kinase Cδ in Complex With Phorbol Ester," Cell 81(6):917-924, Jun. 1995.

\* cited by examiner

US 10,036,067 B2

ISOLATED NUCLEIC ACIDS AND KITS FOR IDENTIFYING SUBJECTS SUSCEPTIBLE TO ATAXIC NEUROLOGICAL DISEASE

CROSS-REFERENCES TO RELATED APPLICATIONS

This application is a divisional of application Ser. No. 10/671,007, filed Sep. 25, 2003, now U.S. Pat. No. 7,655,401, which claims the benefit of Provisional Application No. 60/414,816, filed Sep. 26, 2002, both of which are incorporated herein by reference.

STATEMENT OF GOVERNMENT LICENSE RIGHTS

The present invention was made with government support under Contract No: VISN 20 MIRECC awarded by the Department of Veterans Affairs. The United States government has certain rights in the invention.

FIELD OF THE INVENTION

The present application relates to methods and kits for identifying subjects susceptible to ataxia.

BACKGROUND

The nonepisodic, autosomal dominant, spinocerebellar ataxias (SCA) share the clinical features of progressive incoordination of gait, hand and eye movements and dysarthria, associated with degeneration of the cerebellar cortex and other regions of the central nervous system. Additional features, such as mental retardation, retinopathy, sensory neuropathy or myoclonus are found in some members of the disease family. The incidence of the disease is approximately 1 to 5/100,000, with an average age of onset in the third decade.

There are at least 20 genetically distinct autosomal dominant SCAs (see Mariotti, C., DiDonato, S., "Cerebellar/spinocerebellar syndromes," *Neurol. Sci.* 22:S88-S92 (2001)). Trinucleotide repeat expansions $(CAG)_n$, coding for polyglutamine tracts are responsible for SCA1, SCA2, SCA3, SCA6, SCA7, SCA12 and SCA17, whereas expanded CTG and ATTCT repeats are responsible for SCA8 and SCA10, respectively. In North American populations approximately 30% of SCA families are not linked to the known loci (Moseley et al., *Neurology* 51:1666-1671, 1998).

Given the prevalence of SCA cases not linked to any known genetic loci, there is a need to identify genetic mutations associated with the SCA syndromes that can be used in a genetic screen to identify subjects susceptible to ataxic neurological disease. The present inventors have discovered that individuals with mutations in the protein kinase C gamma ("PRKCG") gene, coding for the protein kinase C gamma protein ("PKCγ"), display an adult onset ataxia.

SUMMARY

In accordance with the foregoing, in one aspect the present invention provides methods of identifying genetic mutations that are associated with ataxic neurological disease in a mammalian subject, the methods comprising identifying a difference between a nucleic acid sequence of a protein kinase C gamma gene from a first mammalian subject exhibiting ataxia and a nucleic acid sequence of a protein kinase C gamma gene from a second mammalian subject which is not exhibiting ataxia, wherein the first and second mammalian subjects are members of the same species, and wherein the difference between the nucleic acid sequences is a genetic mutation that is associated with ataxic neurological disease. In some embodiments of this aspect of the invention, the method further comprises determining whether the identified mutations cosegregate with ataxia.

In another aspect, the present invention provides an isolated nucleic acid molecule encoding a protein kinase C gamma protein comprising a missense mutation selected from the group consisting of R41P, H101Y, S119P, Q127R, G128D, S361G and R597S.

In another aspect, the present invention provides methods of screening a mammalian subject to determine if said subject has a genetic predisposition to develop an ataxic neurological disease, or is suffering from an ataxic neurological disease. The method of this aspect of the invention comprises analyzing the nucleic acid sequence of a protein kinase C gamma gene in a mammalian subject to determine whether a genetic mutation that is associated with an ataxic neurological disease is present in the nucleic acid sequence, wherein the presence of a genetic mutation in the protein kinase C gamma gene that cosegregates with an ataxic neurological disease indicates that the mammalian subject has a genetic predisposition to develop an ataxic neurological disease or is suffering from an ataxic neurological disease.

In another aspect, the invention provides a kit for determining susceptibility or presence of ataxic neurological disease, said kit comprising (i) one or more nucleic acid primer molecules for amplification of a portion of the protein kinase C gamma gene and (ii) written indicia indicating a correlation between the presence of said mutation and risk of ataxic neurological disease. In some embodiments, the kit further comprises means for determining whether a mutation associated with ataxic neurological disease is present. In some embodiments, the kit detects the presence or absence of a mutation in the protein kinase C gamma gene selected from the group consisting of R41P, H101Y, S119P, Q127R, G128D, S361G and R597S.

The invention thus provides methods and kits for identifying genetic mutations in a protein kinase C gamma gene and thereby facilitates diagnosis of ataxic neurological disease and identification of carriers of the genetic defect. The nucleic acid molecules of the invention are useful for as probes to identify genetic mutations in the protein kinase C gamma gene and have therapeutic utility for identifying compounds that can be used to treat ataxic neurological disease.

DETAILED DESCRIPTION

Unless specifically defined herein, all terms used herein have the same meaning as they would to one skilled in the art of the present invention. Practitioners are particularly directed to Sambrook et al. (1989) *Molecular Cloning: A Laboratory Manual,* 2nd ed., Cold Spring Harbor Press, Plainsview, N.Y., and Ausubel et al., *Current Protocols in Molecular Biology,* John Wiley & Sons, New York (1999) for definitions and terms of art.

The following definitions are provided in order to provide clarity with respect to the terms as they are used in the specification and claims to describe the present invention.

As used herein, the term "ataxia" refers to poor coordination of movement and a wide-based, uncoordinated, unsteady gait. Ataxia may result, for example, from dysfunction of the cerebellum and its associated systems, lesions in the spinal cord, peripheral sensory loss, or any combination of these conditions.

As used herein, the term "myoclonus" refers to sudden brief involuntary movements of a muscle or limb.

As used herein, the term "cerebellum" refers to the portion of the brain lying at the back of the skull that is particularly involved with the coordination of movement.

As used herein, the term "nystagmus" refers to involuntary jerky eye movements.

As used herein, the term "dysarthria" refers to difficulty in articulating words.

As used herein, the term "ataxic neurological disease" refers to the clinical manifestation of a slowly progressive incoordination of gait and poor coordination of hand and eye movements which may also be associated with degeneration of the cerebellar cortex and spinal pathways.

As used herein, the term "primer" means a polynucleotide generally having a length of 5 to 50 nucleotides which can serve to initiate a nucleic acid chain extension reaction.

As used herein, the term "protein kinase C gamma (PRKCG) gene" refers to any gene that encodes the PRKCG protein. Some PRKCG genes useful in the practice of this invention are at least 90% identical to the nucleic acid sequence set forth in SEQ ID NO:3. Some PRKCG genes useful in the practice of this invention are at least 95%, or at least 99% identical to the nucleic acid sequence set forth in SEQ ID NO:3.

As used herein, the term "sequence identity" or "percent identical" as applied to nucleic acid molecules is the percentage of nucleic acid residues in a candidate nucleic acid molecule sequence that are identical with a subject nucleic acid molecule sequence (such as the nucleic acid molecule sequence set forth in SEQ ID NO:3), after aligning the sequences to achieve the maximum percent identity, and not considering any nucleic acid residue substitutions as part of the sequence identity. No gaps are introduced into the candidate nucleic acid sequence in order to achieve the best alignment. Nucleic acid sequence identity can be determined in the following manner. The subject polynucleotide molecule sequence is used to search a nucleic acid sequence database, such as the Genbank database, using the program BLASTN version 2.1 (based on Altschul et al., *Nucleic Acids Research* 25:3389-3402 (1997)). The program is used in the ungapped mode. Default filtering is used to remove sequence homologies due to regions of low complexity as defined in Wootton, J. C. and S. Federhen, *Methods in Enzymology* 266:554-571 (1996). The default parameters of BLASTN are utilized.

As used herein, the term "genetic mutation" is an alteration of the wild-type protein kinase C gamma (PRKCG) sequence deposited in GenBank, provided as SEQ ID NO:3 that is not a recognized polymorphism (i.e., has a population frequency less than 1% in mammalian control subjects of the same species that do not exhibit ataxia).

In one aspect, the present invention provides methods of identifying genetic mutations that are associated with ataxic neurological disease in a mammalian subject. The methods of this aspect of the invention comprise the step of identifying a difference between a nucleic acid sequence of a protein kinase C ("PRKCG") gene from a first mammalian subject exhibiting ataxia and a nucleic acid sequence of a PRKCG gene from a second mammalian subject which is not exhibiting ataxia, wherein the first and second mammalian subjects are members of the same species, and wherein the difference between the nucleic acid sequences is a genetic mutation that is associated with ataxic neurological disease. In some embodiments, the method further comprises the step of determining whether the identified genetic mutation cosegregates with ataxia.

The methods of this aspect of the invention are useful to identify genetic mutations associated with ataxic neurological disease in any mammalian subject, particularly human subjects. For example, the methods of the invention may be used to identify genetic mutations in the PRKCG gene that are associated (i.e., where the mutation is found to occur in subjects predisposed to develop ataxic neurological disease and the mutation is not found in subjects not predisposed to develop ataxic neurological disease) with the occurrence of ataxic neurological disease in individuals at risk for developing this disease.

The present inventors have discovered that mutations in the PRKCG gene locus are responsible for a portion of cases of ataxic neurological disease not attributed to SCA1, 2, 3 and 6. PRKCG was identified as a candidate gene based in part on chromosomal mapping to a 22 cM region on chromosome 19q13.4-qter as described in Example 1. PKCγ is a member of the conventional subgroup (cPKC) of a serine/threonine kinase family (Coussens et al., *Science* 233:859-866 (1986); Knopf et al., *Cell* 46:491-502 (1986)) that plays a role in such diverse processes as signal transduction, cell proliferation and differentiation, synaptic transmission and tumor promotion (see Tanaka and Nishizuka, *Annu. Rev. Neurosci.* 17:551-567 (1994)).

The amino-terminal regulatory domain of PKCγ contains two cysteine-rich regions (cys1 and cys2), collectively termed C1, each of which interacts with two zinc ions and provides high affinity diacylglycerol (DAG)/phorbol ester binding, and a $Ca^{2+}$ sensitive region (C2) (reviewed in Newton A. C., *Chem. Rev.* 101:2353-2364 (2001)). The carboxyl-terminal catalytic domain contains kinase and substrate recognition regions.

The PRKCG human gene encompasses 24 kilobases and consists of 18 exons. The PRKCG cDNA coding sequence is provided herein as SEQ ID NO:1 which corresponds to nucleotides 187-2280 of GenBank accession number NM_002739. Disclosed herein are nucleic acid mutations numbered sequentially with respect to the first nucleotide of SEQ ID NO:1. The PKCγ protein encoded by SEQ ID NO:1 is provided herein as SEQ ID NO:2. Disclosed herein are amino acid mutations numbered sequentially with respect to the first amino acid residue of SEQ ID NO:2. The entire 25 kilobase genomic locus that encompasses the PRKCG gene is provided herein as SEQ ID NO:3. With respect to the first nucleotide in SEQ ID NO:3, the 18 exons are as follows: exon 1: nucleotides 440 to 609; exon 2: nucleotides 1108 to 1139; exon 3: 2106 to 2188; exon 4: nucleotides 7583 to 7694; exon 5: nucleotides 7831 to 7962; exon 6: nucleotides 9619 to 9775; exon 7: nucleotides 10454 to 10588; exon 8: nucleotides 10933 to 11020; exon 9: nucleotides 11307 to 11336; exon 10: nucleotides 15904 to 16056; exon 11: nucleotides 16385 to 16573; exon 12: nucleotides 18178 to 18269; exon 13: nucleotides 18364 to 18426; exon 14: nucleotides 18556 to 18694; exon 15: nucleotides 21018 to 21098; exon 16: nucleotides 22580 to 22687; exon 17: nucleotides 24262 to 24402; and exon 18: nucleotides 24652 to 24840.

The present inventors have identified several missense mutations (for example, H101Y, S119P, and G128D) in the Cys2 region of the C1 domain of PKCγ (SEQ ID NO:2) that cause a disease that is clinically indistinguishable from other "uncomplicated" SCAs (see Example 1, Example 2 and Chen et al., *Am. J. Hum. Genet.* 72:839-849, 2003, incorporated herein by reference). The patients with mutations in PRKCG (as described in Examples 1 and 2) displayed an adult-onset cerebellar ataxia without any differentiating features such as cognitive decline, visual or other sensory loss, axial myoclonus or peripheral neuropathy. The practice of this aspect of the invention is therefore useful to identify additional mutations in the PRKCG gene that are associated with ataxic neurological disease.

In the practice of this aspect of the method of the invention, any method of obtaining reliable nucleic acid sequence data from a mammalian subject exhibiting ataxia may be utilized. For example, reliable sequence data may be obtained from existing databases of sequence data, or alternatively, a reliable nucleic acid assay that will identify a genetic mutation in the PRKCG may be utilized.

In one embodiment of the methods of the invention, a genetic mutation is detected by amplification of all or part of the PRKCG gene from genomic DNA followed by sequencing of the amplified DNA. For example, each of the 18 exons of the PRKCG gene may be amplified individually or in combination using as template genomic DNA from a test subject exhibiting ataxia. A method of amplification which is well known by those skilled in the art is the polymerase chain reaction (PCR) (see *Current Protocols in Molecular Biology*, Ausubel, F. M. et al., John Wiley & Sons; 1995). Alternative amplification techniques may also be used in the method of this aspect of the invention, such as the ligase chain reaction (LCR) (Wu and Wallace, *Genomics* 4:560-569 (1989)), strand displacement amplification (SDA) (Walker et al., *Proc. Nat'l. Acad. Sci. USA* 89:392-396 (1992)), self-sustained sequence replication (3SR) (Fahy et al., *PCR Methods Appl.* 1:25-33 (1992)), and Branched Chain Amplification which are known and available to persons skilled in the art.

The PCR process involves the use of pairs of primers, one for each complementary strand of the duplex DNA (wherein the coding strand is referred to as the "sense strand" and its complementary strand is referred to as the "anti-sense strand"), that will hybridize at sites located on either side of a region of interest in a gene. Chain extension polymerization is then carried out in repetitive cycles to increase the number of copies of the region of interest exponentially. Primers useful in the practice of the method of the invention comprise polynucleotides that hybridize to a region of a PRKCG gene, which can serve to initiate a chain extension reaction. A "primer pair" is a pair of primers which specifically hybridize to sense (coding) and antisense (non-coding) strands of a duplex polynucleotide to permit amplification of the region lying between the primers of the pair. Primers useful in the practice of this aspect of the invention comprise a polynucleotide ranging from 5 to 50 bp of continuous sequence chosen from SEQ ID NO:1 or SEQ ID NO:3. For example, primer pairs suitable for PCR amplification and sequencing of each of the 18 exons in PRKCG are described in TABLE 1 and TABLE 2. TABLE 1 describes SEQ ID NOS: 4-35 which are primers useful for amplification and sequencing the PRKCG gene in the practice of the method of the invention. The first column of TABLE 1 describes the SEQ ID NO, the second column provides the nucleotide sequence of the primer, and the third column provides the exon name given to the primer. TABLE 2 describes sets of primers useful for PCR amplifying the 18 exons of the PRKCG gene from genomic DNA. The first column of TABLE 2 describes the exon to be amplified, and the second and third columns provide the forward and reverse primers used to amplify the exon. Tm refers to the melting temperature of the oligonucleotide pair. The expected PCR product size in base pairs (bp) for each PCR amplification is provided in the fifth column. The right side of TABLE 2 provides a set of primers useful for sequencing across each exon. Example 1 provides a non-limiting example of this embodiment of the method of the invention.

In one embodiment of the method of the invention, after amplification, genetic mutations are detected in the amplified DNA by sequence analysis. Methods of DNA sequence analysis are well known in the art. A well known method of sequencing is the "chain termination" method first described by Sanger et al., *PNAS (USA)* 74(12):5463-5467 (1977) and detailed in SEQUENASE™ 2.0 product literature (Amersham Life Sciences, Cleveland). Sequencing can be performed using a single primer or a primer pair. Primers are chosen for sequencing based on their proximity to the region of interest. Non-limiting examples of suitable sequencing primers for each exon are described in TABLE 1 and TABLE 2.

TABLE 1

| SEQ ID # | Oligo primer SEQ 5'-3' | Exon |
|---|---|---|
| 4 | ctgcctttggctcttcct | 1F |
| 5 | taggagtctgcacccctagt | 1R |
| 6 | ctggattcctgggtctgaag | 2F |
| 7 | cagcctccaccctcctga | 2R |
| 8 | cgctctctcttttccaatttt | 3F |
| 9 | gaggaggagaaccaggtgt | 3R |
| 10 | caaggcaggaggaaaagata | 4F |
| 11 | atttcccggaacccagac | 4R |
| 12 | catgaaatgctcctgtgagt | 5F |
| 13 | acaagtgccttgggtcag | 5R |
| 14 | gcttggaactcttgattgct | 6F |
| 15 | ccactaggaccctcagatca | 6R |
| 16 | acctccagcaccaaggat | 7F |
| 17 | cacacacagatggagatggt | 7R |
| 18 | cttccaatgtctttgcctct | 8F |
| 19 | atgtgtggggaattgaagac | 9R |
| 20 | ttgggagcatttccttatcg | 10F |
| 21 | aaatctgaccttcccacaga | 10R |
| 22 | tcccttaagagatggaggaa | 11F |
| 23 | ctcgccctaaactcagaatc | 11R |
| 24 | gtctgatagttggcggtggt | 12F |
| 25 | agaaggtcagtggctggat | 12R |
| 26 | atccagccactgaccttct | 13F |
| 27 | cagtgccaagctcacctg | 14R |
| 28 | gggaagagcttgtgctgaaa | 15F |
| 29 | ctaactggctcctcctgaga | 15R |
| 30 | ggcatccgagataggaaatg | 16F |

TABLE 1-continued

| SEQ ID # | Oligo primer SEQ 5'-3' | Exon |
|---|---|---|
| 31 | tcaggaatgggagcattttt | 16R |
| 32 | ttctctgggtctacctgtcc | 17F |
| 33 | gtgtctgcacctccttttgt | 17R |
| 34 | cagacaccatgaagcatgaata | 18F |
| 35 | ttagtggtgtggtctctgga | 18R |

TABLE 2

PRIMERS FOR EXON FRAGMENT AMPLIFICATION AND SEQUENCING OF PRKCG GENE

| | PCR AMPLIFICATION | | | | SEQUENCING REACTION | | |
|---|---|---|---|---|---|---|---|
| Exon | Forward | Reverse | Tm | Size bp | Exon | Forward | Reverse |
| 1 + 2 | 1F (SEQ ID NO: 4) | 2R (SEQ ID NO: 7) | 62 | 1016 | 1 | 1F (SEQ ID NO: 4) | 1R (SEQ ID NO: 5) |
| | | | | | 2 | 2F (SEQ ID NO: 6) | 2R (SEQ ID NO: 7) |
| 3 | 3F (SEQ ID NO: 8) | 3R (SEQ ID NO: 9) | 56 | 203 | 3 | 3F (SEQ ID NO: 8) | 3R (SEQ ID NO: 9) |
| 4 + 5 | 4F (SEQ ID NO: 10) | 5R (SEQ ID NO: 13) | 60 | 542 | 4 | 4F (SEQ ID NO: 10) | 4R (SEQ ID NO: 11) |
| | | | | | 5 | 5F (SEQ ID NO: 12) | 5R (SEQ ID NO: 13) |
| 6 | 6F (SEQ ID NO: 14) | 6R (SEQ ID NO: 15) | 56 | 310 | 6 | 6F (SEQ ID NO: 14) | 6R (SEQ ID NO: 15) |
| 7 + 8 + 9 | 7F (SEQ ID NO: 16) | 9R (SEQ ID NO: 19) | 60 | 1059 | 7 | 7F (SEQ ID NO: 16) | 7R (SEQ ID NO: 17) |
| | | | | | 8 + 9 | 8F (SEQ ID NO: 18) | 9R (SEQ ID NO: 19) |
| 10 + 11 | 10F (SEQ ID NO: 20) | 11R (SEQ ID NO: 23) | 56 | 825 | 10 | 10F (SEQ ID NO: 20) | 10R (SEQ ID NO: 21) |
| | | | | | 11 | 11F (SEQ ID NO: 22) | 11R (SEQ ID NO: 23) |
| 12 + 13 + 14 | 12F (SEQ ID NO: 24) | 14R (SEQ ID NO: 27) | 60 | 896 | 12 | 12F (SEQ ID NO: 24) | 12R (SEQ ID NO: 25) |
| | | | | | 13 + 14 | 13F (SEQ ID NO: 26) | 14R (SEQ ID NO: 27) |
| 15 + 16 | 15F (SEQ ID NO: 28) | 16R (SEQ ID NO: 31) | 56 | 1880 | 15 | 15F (SEQ ID NO: 28) | 15R (SEQ ID NO: 29) |
| | | | | | 16 | 16F (SEQ ID NO: 30) | 16R (SEQ ID NO: 31) |
| 17 + 18 | 17F (SEQ ID NO: 32) | 18R (SEQ ID NO: 35) | 56 | 932 | 17 | 17F (SEQ ID NO: 32) | 17R (SEQ ID NO: 33) |
| | | | | | 18 | 18F (SEQ ID NO: 34) | 18R (SEQ ID NO: 35) |

Once the nucleic acid sequence from the test subject is obtained, the sequence is compared to the nucleic acid sequence of one or more subjects not exhibiting ataxia in order to identify genetic mutations that are associated with ataxia. For example, resulting sequences can be aligned with the known exon sequence using a multiple sequence alignment tool, Sequencher (Gene Codes Corporation, Ann Arbor, Mich.), in order to identify any nucleotide changes as described in Example 4. In one embodiment, the information and analysis can be recorded on a database and the comparisons can be performed by a computer system accessing said database. In this manner, the amplified sequences of PRKCG from a subject exhibiting ataxia are sequenced until a mutation associated with ataxia is identified.

A mutation associated with ataxia encompasses any alteration of the wild-type protein kinase C gamma (PRKCG) sequence deposited in GenBank, provided as SEQ ID NO:3, that is not a recognized polymorphism (i.e., has a population frequency less than 1% in mammalian control subjects of the same species that do not exhibit ataxia). A genetic mutation may be any form of sequence alteration including a deletion, insertion, point mutation or DNA rearrangement in the coding or noncoding regions. Deletions may be small or large and may be of the entire gene or of only a portion of the gene. Point mutations may result in stop codons, frameshift mutations or amino acid substitutions. Point mutations may also occur in regulatory regions, such as in the promoter of the PRKCG gene, leading to loss or diminution of expression of the mRNA. Point mutations may also abolish proper RNA processing, leading to loss of expression of the PRKCG gene product, or to a decrease in mRNA stability or translation efficiency. DNA rearrangements include a simple inversion of a single segment of DNA, a reciprocal or nonreciprocal translocation disrupting any portion of the gene, or a more complex rearrangement. The following characteristics are supportive, but are not required for a genetic mutation to be a causative mutation for ataxic neurological disease: 1) the change results in an amino acid substitution in a highly evolutionarily conserved residue; 2) the change occurs in a functional domain; 3) the change is predicted to affect splicing; or 4) the change cosegregates with disease in a family (where applicable).

In one embodiment of this aspect of the method of the invention, once a mutation is identified in a subject exhibiting ataxia, co-segregation analysis is carried out to determine if the particular mutation in the PRKCG gene co-segregates with the presence of ataxic neurological disease symptoms in the subjects tested. Co-segregation analysis can be done in several ways. In one embodiment, co-segregation analysis is done by sequencing DNA amplified from the corresponding exon in subjects exhibiting ataxia utilizing the previously described methods. For example, DNA sequence variations can be identified using DNA sequencing, as described in Example 1. Alternatively, there are several other methods that can be used to detect and confirm DNA sequence variation including, for example, (1) single stranded conformation analysis (SSCA) (Orita et al., Proc. Nat'l. Acad. Sci. USA 86:2776-2770 (1989)); (2) denaturing gradient gel electrophoresis (DGGE) based on the detection of mismatches between the two complementary DNA strands (Wartell et al., Nucl. Acids Res. 18: 2699-2705 (1990)); (3) RNase protection assays (Finkelstein et al., Genomics 7:167-172 (1990)); (4) hybridization with allele-specific oligonucleotides (ASOs) (Conner et al., Proc. Nat'l. Acad. Sci. USA 80:278-282 (1983)) and (5) allele-specific PCR (Rano & Kidd, Nucl. Acids Res. 17:8392 (1989)). In the SSCA, DGGE and RNase protection assay, a new electrophoretic band appears when a mutation is present. SSCA detects a band which migrates differently because the sequence change causes a difference in single-strand, intramolecular base pairing. DGGE detects differences in migration rates of mutant sequences compared to wild-type sequences using a denaturing gradient gel. For allele-specific PCR, primers are used which hybridize at their 3' ends to a particular PRKCG mutation. If the particular PRKCG mutation is not present, an amplification product is not observed. Insertions and deletions of genes can also be detected by cloning, sequencing and amplification.

In another embodiment, genetic mutations are identified by hybridization of amplified regions of the PRKCG gene with allele-specific oligonucleotides. For example, a hybridization assay may be carried out by isolating genomic DNA from a mammalian subject exhibiting ataxia, hybridizing a DNA probe onto said isolated genomic DNA, said DNA probe spanning said mutation in said gene, wherein said DNA probe is capable of detecting said mutation; treating said genomic DNA to determine the presence or absence of said DNA probe and thereby indicating the presence or absence of said genetic mutation. Desirable probes useful in such a DNA hybridization assay comprise a nucleic acid sequence that is unique to the genetic mutation. Analysis can involve denaturing gradient gel electrophoresis or denaturing HPLC methods, for example. For guidance regarding probe design and denaturing gel eletrophoresis or denaturing HPLC methods, see, e.g., Ausubel et al., 1989, *Current Protocols in Molecular Biology*, Green Publishing Associates and Wiley Interscience, N.Y.

In another embodiment of this aspect of the method of the invention, restriction fragment length polymorphism (RFLP) for the gene can be used to score for a genetic mutation in a co-segregation analysis. RFLP has been described in U.S. Pat. Nos. 4,965,188; 4,800,159, incorporated herein by reference. In this technique, restriction enzymes are used which provide a characteristic pattern of restriction fragments, wherein a restriction site is either missing or an additional restriction site is introduced in the mutant allele. Thus, DNA from an individual and from control DNA sequences are isolated and subjected to cleavage by restriction enzymes which are known to provide restriction fragments which differentiate between normal and mutant alleles, and the restriction patterns are identified. Example 3 further illustrates RFLP methods that are useful in the practice of the method of the invention.

Several genetic mutations in PRKCG that are associated with ataxia have been identified by practicing the methods of this aspect of the invention as described in Examples 1-3 and shown in TABLE 3. TABLE 3 provides a list of mutations identified in a PRKCG gene using the methods of this aspect of the invention. The first column of TABLE 3 describes the exon the mutation resides in, the second column describes the nucleotide change in the cDNA (numbered sequentially with reference to SEQ ID NO:1) for each mutant, the third column describes the type of mutation that is present (missense, silent, deletion, etc.), the fourth column describes primer pairs useful to PCR amplify the exon containing the mutation and the fifth column describes primers useful for sequencing across the region containing the mutation.

In another aspect, the present invention provides isolated nucleic acid molecules encoding a protein kinase C gamma protein comprising a mutation selected from the group consisting of R41P, H101Y, S119P, Q127R, G128D, S361G and R597S. The mutations in the PKCγ protein are numbered sequentially with respect to the first amino acid of SEQ ID NO:2. The nucleotide sequences are numbered sequentially according to the first nucleotide of SEQ ID NO:1. Each mutation is further described as follows:

Mutation R41P results from a nucleotide change of G to C at nucleotide 122, which results in the codon change CGC to CCC which in turn results in the missense mutation at amino acid R41 to P, substituting a proline for an arginine at amino acid residue 41.

Mutation H101Y results from a nucleotide change of C to T at nucleotide 301, which results in the codon change CAC to TAC which in turn results in the missense mutation at amino acid H101 to Y, substituting a tyrosine for a histidine at amino acid residue 101.

Mutation S119P results from a nucleotide change of T to C at nucleotide 355, which results in the codon change TCC to CCC which in turn results in the missense mutation at amino acid S119 to P, substituting a proline for a serine at amino acid residue 119.

Mutation Q127R results from a nucleotide change of A to G at nucleotide 380, which results in the codon change CAG to CGG which in turn results in the missense mutation at amino acid Q127 to R, substituting an arginine for a glutamine at amino acid residue 127.

Mutation G128D results from a nucleotide change of a G to A at nucleotide 383, which results in the codon change GGC to GAC which in turn results in the missense mutation at amino acid G128 to D, substituting an aspartic acid for a glycine at amino acid residue 128.

Mutation S361G results from a nucleotide change of an A to G at nucleotide 1081, which results in the codon change AGT to GGT which in turn results in the missense mutation at amino acid S361 to G, substituting a glycine for a serine at amino acid residue 361.

Mutation R597S results from a nucleotide change of a C to A at nucleotide 1789, which results in the codon change CGC to AGC which in turn results in the missense mutation at amino acid R597 to S, substituting a serine for an arginine at amino acid residue 597.

In this regard, in some embodiments the isolated nucleic acid molecules described herein are at least 90% identical to a portion of SEQ ID NO:1 or its complement. In some embodiments, the isolated nucleic acid molecules described herein are at least 90% identical to a portion of SEQ ID NO:3 or its complement. In some embodiments, the isolated nucleic acid molecules described herein hybridize to the complement of SEQ ID NO:1 under conditions of 5×SSC at 50° C. for 1 hr. In some embodiments, the isolated nucleic acid molecules described herein hybridize to the complement of SEQ ID NO:1 under conditions of 5×SSC at 60° C. for 1 hr. In some embodiments, the isolated nucleic acid molecules described herein hybridize to the complement of SEQ ID NO:3 under conditions of 5×SSC at 50° C. for 1 hr. In some embodiments, the isolated nucleic acid molecules described herein hybridize to the complement of SEQ ID NO:3 under conditions of 5×SSC at 60° C. for 1 hr.

Some nucleic acid embodiments, for example, include genomic DNA, RNA and cDNA encoding the mutant proteins or fragments thereof. In some embodiments, the invention also encompasses DNA vectors such as, for example DNA expression vectors that contain any of the foregoing nucleic acid sequences operatively associated with a regulatory element that directs the expression of the coding sequences the nucleic acids above, and genetically engineered host cells that contain any of the foregoing nucleic acid sequences operatively associated with a regulatory element that directs the expression of the coding sequences in the host cell. The nucleic acids encoding the protein kinase C gamma protein mutations can be manipulated using conventional techniques in molecular biology so as to create recombinant constructs that express mutant polypeptides.

The nucleic acid sequences described above have diagnostic as well as therapeutic use. The nucleic acid sequences can be used as probes to identify more genetic mutations in the PRKCG gene and to detect the presence or absence of wild type or mutant genes in an individual, such as in nucleic acid hybridization assays, southern and northern blot analysis, and as controls for screening assays and the kits described herein. The sequences described herein can also be incorporated into constructs for preparing recombinant mutant proteins or used in methods of searching or identifying agents that modulate PRKCG levels and/or activity, for example, candidate therapeutic agents. Because the mutations of this aspect of the invention are dominant negative or gain of function mutations, they have also have therapeutic utility for use in the identification and development and design of drugs which circumvent or overcome the mutated PRKCG gene function. The sequences of the nucleic acids and/or proteins described herein can also be incorporated into computer systems and used with modeling software so as to enable rational drug design. Information from genotyping methods provided herein can be used, for example, in computer systems, in pharmacogenomic profiling of therapeutic agents to predict effectiveness of an agent in treating an individual for an ataxic neurological disease.

The identification of mutant H101Y is described in Example 1. The identification of mutants R41P and S119P are described in Example 2. The identification of mutants Q127R, G128D, S361G and R597S are described in Example 4. The use of missense mutation H101Y to screen for ataxic neurological disease is further described in Example 1. The use of missense mutations S119P and G128D are further described in Example 2. The characterization of these mutations is described in TABLE 3.

In another aspect, the present invention provides methods of screening a mammalian subject to determine if said subject has a genetic predisposition to develop an ataxic neurological disease, or is suffering from an ataxic neurological disease. The methods of this aspect of the invention comprise the step of analyzing the nucleic acid sequence of a PRKCG gene in a subject to determine whether a genetic mutation that is associated with an ataxic neurological disease is present in the nucleic acid sequence, wherein the presence of such a mutation indicates that the mammalian subject has a genetic predisposition to develop ataxic neurological disease or is diagnosed as suffering from such as disease. In some embodiments, the method further comprises determining whether the mammalian subject is exhibiting ataxia. The clinical examination of a mammalian subject for symptoms related to ataxia may be done either prior to, or after nucleic acid analysis of the test subject.

The method of this aspect of the invention is useful for screening any mammalian subject, such as for example, a human subject, for the genetic predisposition to develop ataxic neurological disease. The method is especially useful for screening and diagnosing presymptomatic at-risk family members for the presence or absence of mutations associated with the disease. The method is also useful for screening subjects exhibiting ataxia to determine whether their symptoms are caused by a genetic mutation in the PRKCG gene.

Any genetic mutation in the PRKCG gene that cosegregates with an ataxic neurological disease is useful in the practice of the method of this aspect of the invention. Examples of such mutations are shown in TABLE 3.

TABLE 3

Mutations Identified in the PRKCG Gene

| exon | nucleotide change in cDNA | Predicted amino acid change in protein | Type of mutation | Primers used to PCR amplify | Primers used to sequence |
|---|---|---|---|---|---|
| 1 | 122G to C | R41P | missense | 1F (SEQ ID NO: 4); 2R (SEQ ID NO: 7) | 1F (SEQ ID NO: 4); 1R (SEQ ID NO: 5) |
| 3 | 204C to G | V68V | silent* | 3F (SEQ ID NO: 8); 3R (SEQ ID NO: 9) | 3F (SEQ ID NO: 8); 3R (SEQ ID NO: 9) |
| 3 | 207C to T | C69C | silent** | 3F (SEQ ID NO: 8); 3R (SEQ ID NO: 9) | 3F (SEQ ID NO: 8); 3R (SEQ ID NO: 9) |
| 3 | 225A to G | R75R | silent* | 3F (SEQ ID NO: 8); 3R (SEQ ID NO: 9) | 3F (SEQ ID NO: 8); 3R (SEQ ID NO: 9) |
| 3 | 285C to T (last nucleotide of exon 3) | D95D | silent, but alters the splice coefficient | 3F (SEQ ID NO: 8); 3R (SEQ ID NO: 9) | 3F (SEQ ID NO: 8); 3R (SEQ ID NO: 9) |
| 4 | 296-301 del | del 100K, 101H | deletion | 4F (SEQ ID NO: 10); 5R (SEQ ID NO: 13) | 4F (SEQ ID NO: 10); 4R (SEQ ID NO: 11) |
| 4 | 301C to T | H101Y | missense | 4F (SEQ ID NO: 10); 5R (SEQ ID NO: 13) | 4F (SEQ ID NO: 10); 4R (SEQ ID NO: 11) |
| 4 | 355T to C | S119P | missense | 4F (SEQ ID NO: 10); 5R (SEQ ID NO: 13) | 4F (SEQ ID NO: 10); 4R (SEQ ID NO: 11) |
| 4 | 380A to G | Q127R | missense | 4F (SEQ ID NO: 10); 5R (SEQ ID NO: 13) | 4F (SEQ ID NO: 10); 4R (SEQ ID NO: 11) |
| 4 | 383G to A | G128D | missense | 4F (SEQ ID NO: 10); 5R (SEQ ID NO: 13) | 4F (SEQ ID NO: 10); 4R (SEQ ID NO: 11) |
| 6 | 672T to C | N224N | silent** | 6F (SEQ ID NO: 14); 6R (SEQ ID NO: 15) | 6F (SEQ ID NO: 14); 6R (SEQ ID NO: 15) |

TABLE 3-continued

Mutations Identified in the PRKCG Gene

| exon | nucleotide change in cDNA | Predicted amino acid change in protein | Type of mutation | Primers used to PCR amplify | Primers used to sequence |
|---|---|---|---|---|---|
| 10 | 1081A to G | S361G | missense | 10F (SEQ ID NO: 20); 11R (SEQ ID NO: 23) | 10F (SEQ ID NO: 20); 10R (SEQ ID NO: 21) |
| 12 | 1284C to T | D428D | silent* | 12 (SEQ ID NO: 24); 14R (SEQ ID NO: 27) | 12F (SEQ ID NO: 24); 12R (SEQ ID NO: 25) |
| 16 | 1677C to T | D559D | silent* | 15F (SEQ ID NO: 28); 16R (SEQ ID NO: 31) | 16F (SEQ ID NO: 30); 16R (SEQ ID NO: 31) |
| 16 | 1683G to A | E561E | silent* | 15F (SEQ ID NO: 28); 16R (SEQ ID NO: 31) | 16F (SEQ ID NO: 30); 16R (SEQ ID NO: 31) |
| 17 | 1789C to A | R597S | missense | 17F (SEQ ID NO: 32); 18R (SEQ ID NO: 35) | 17F (SEQ ID NO: 32); 17R (SEQ ID NO: 33) |

*Silent mutations that have been detected in only one affected person and have not been observed in any of more than 200 other individuals
**Silent mutations that have been detected in more than one affected person but have not previously been reported in the database as a polymorphism In one embodiment, genetic mutations that cosegregate with an ataxic neurological disease are missense mutations in which a nucleic acid base change results in an amino acid substitution in the PRKCG protein. Examples of such missense mutations include, for example, R41P, H101Y, S119P, Q127R, G128D, S361G, and R597S as shown in TABLE 3.

In another embodiment, the method of this aspect of the invention can be practiced using mutations that cause deletions, such as, for example, the deletion mutation identified in exon 4, shown in TABLE 3 which deletes nucleotides 296-301. Silent mutations which do not alter the amino acid sequence, but change splicing or gene regulation may also be used, such as for example, the mutation in exon 3 shown in TABLE 4 which changes nucleotide 285C to T, thereby altering the splicing coefficient of the PRKCG mRNA.

In some embodiments of the method of this aspect of the invention, subjects are screened for genetic mutations at one or more of the protein positions: 41, 101, 119, 127, 128, 361 or 597.

In some embodiments of this aspect of the method of the invention, subjects are screened for the presence of a genetic mutation that is associated with an ataxic neurological disease in exon 4 of a PRKCG gene, such as, for example, nucleotides 7583 to 7694 of SEQ ID NO: 3. Exon 4 encodes a region of highly conserved amino acid residues in the cys2 region of PRKCG gene. Examples of mutations found in exon 4 that cosegregate with ataxic neurological disease are shown in TABLE 3 and include H101Y, S199P, G128D, and Q127R.

Individuals carrying particular mutations in the PRKCG gene may be identified using a variety of techniques of analyzing nucleic acid sequence that are well known in the art such as, for example, direct sequencing, PCR amplification and sequencing, restriction fragment length polymorphism (RFLP), nucleic acid hybridization, and single strand conformation polymorphism (SSCP). For each of these techniques, the test subject provides a biological sample containing genomic DNA to be analyzed. The test sample may be obtained from body cells, such as those present in peripheral blood, urine, saliva, surgical specimen, and autopsy specimens. The test sample can be processed to inactivate interfering compounds, and to purify or partially purify the nucleic acids in the sample. Any suitable purification method can be employed to obtain purified or partially purified nucleic acids from the test sample. A lysing reagent optionally can be added to the sample, particularly when the nucleic acids in the sample are sequestered or enveloped, for example, by cellular or nuclear membranes. Additionally, any combination of additives, such as buffering reagents, suitable proteases, protease inhibitors, nucleases, nuclease inhibitors and detergents can be added to the sample to improve the amplification and/or detection of the nucleic acids in the sample. Additionally, when the nucleic acids in the sample are purified or partially purified, the use of precipitation can be used, or solid support binding reagents can be added to or contacted to the sample, or other methods and/or reagents can be used. One of ordinary skill in the art can routinely select and use additives for, and methods for preparation of a nucleic acid sample for amplification.

In one embodiment of the method of the invention, the nucleic acid sequence is analyzed by direct sequencing for differences in nucleic acid sequence from the wild-type PRKCG gene by sequencing of the subject's PRKCG gene using primers specific for the region of interest, such as, for example, the sequencing primers described in TABLE 1 and TABLE 2.

In another embodiment, prior to sequencing the DNA is amplified enzymatically in vitro through use of PCR (Saiki et al., Science 239:487-491 (1988)) or other in vitro amplification methods as previously described herein. In a further embodiment, the DNA from an individual can be evaluated using RFLP techniques are described in Example 3 and elsewhere herein. The previously described methods useful for determining co-segregation analysis are also useful in this aspect of the method of the invention, such as, for example, nucleic acid hybridization techniques and single strand conformation polymorphism (SSCP). SSCP is a rapid and sensitive assay for nucleotide alterations, including point mutations (see Orita, M., et al., Genomics 5:874-879 (1989). DNA segments ranging in length from approximately 100 bp to approximately 400 bp are amplified by PCR, heat denatured and electrophoresed on high resolution-non-denaturing gels. Under these conditions, each single-stranded DNA fragment assumes a secondary structure determined in part by its nucleotide sequence. Even single base changes can significantly affect the electrophoretic mobility of the PCR product.

In another aspect, the present invention provides kits for determining susceptibility or presence of ataxic neurological disease in a subject. The kits of the invention include (i) one or more nucleic acid primer molecules for amplification of a portion of the PRKCG gene, and (ii) written indicia indicating a correlation between the presence of said mutation and risk of ataxic neurological disease. In one embodiment, the kits of the invention further comprise means for determining whether a mutation associated with ataxic neurological disease is present. In some embodiments, the kits of the invention comprise detection components specific for one or more of the particular genetic mutations described herein.

Primer molecules for amplification of a portion of the PRKCG gene can be of any suitable length and composition and are selected to facilitate amplification of at least one or more regions (in the case of duplexed or multiplexed amplification) of the PRKCG as shown in SEQ ID NO: 3 that potentially contains a genetic mutation. For example, oligonucleotide primers can be in the range of 5 bp to 50 bp or longer, and are chosen as primer pairs so that primers hybridize to sequences flanking the putative mutation. Primer pairs typically have an annealing temperature within about 20° C. of each other. Computer programs are useful in the design of primers with the required specificity and optimal amplification properties. See, e.g., Oligo version 5.0 (available from National Biosciences Inc., 3001 Harbor Lane, Suite 156, Plymouth Minn.). Examples of primer pairs suitable for inclusion in the kit of the invention are provided in TABLE 2.

Similarly, a kit of the invention can also provide reagents for a duplexed amplification reaction (with two pairs of primers) a multiplexed amplification reaction (with three or more pair of primers) so as to amplify multiple sites of PRKCG nucleotide mutations in one reaction.

Also included in the kit of the invention are written indicia indicating a correlation (typically a positive correlation) between the presence of a particular mutation in the PRKCG gene and the risk of ataxic neurological disease.

The kit optionally also comprises one or more enzymes useful in the amplification or detection of nucleic acids and/or nucleotide sequences. Suitable enzymes include DNA polymerases, RNA polymerases, ligases, and phage replicases. Additional suitable enzymes include kinases, phosphatases, endonucleases, exonucleases, RNAses specific for particular forms of nucleic acids (including, but not limited to, RNAse H), and ribozymes. Other suitable enzymes can also be included in the kit.

The kit optionally comprises amplification reaction reagents suitable for use in nucleic acid amplification. Such reagents are well know and include, but are not limited to: enzyme cofactors such as magnesium or manganese; salts; nicotinamide adenine dinucleotide (NAD), and deoxynucleoside triphosphates (dNTPs). The kit optionally can also comprise detection reaction reagents, such as light or fluorescence generating substrates for enzymes linked to probes.

The kit optionally includes control DNA, such as positive and negative control samples. Negative control samples may comprise for example, genomic DNA or PRKCG cDNA from a mammalian subject with no predisposition to ataxic neurological disease, or portions thereof. Positive control samples may comprise, for example, nucleic acid molecules containing an identified mutation in the PRKCG gene as described herein.

The kit optionally includes instructions for using the kit in the detection of mutations in PRKCG associated with ataxic neurological disease. The kit also preferably includes instructions on the appropriate parameters for the amplification reaction. Any suitable set of amplification parameters can be employed. For example, the precise temperature at which double-stranded nucleic acid sequences dissociate, primers hybridize or dissociate, and polymerase is active, are dependent on the length and composition of the sequences involved, the salt content of the reaction, the oligonucleotide concentration, the viscosity of the reaction and the type of polymerase. One of ordinary skill in the art can easily determine appropriate temperatures for the amplification reaction (see, e.g., Wetmur, *J. Critical Reviews in Biochemistry and Molecular Biology* 26:227-59 (1991). For example, temperatures above about 90° C., such as between about 92° C., and about 100° C., are typically suitable for the dissociation of double-stranded nucleic acid sequences. Temperatures for forming primer hybrids are preferably between about 45° C. and about 65° C. Temperatures for the polymerization/extension phase are typically between about 60° C. and about 90° C., depending on the polymerase utilized in the reaction.

A multiplicity of suitable methods may be used to analyze the amplified nucleic acid product to determine whether a mutation associated with ataxic neurological disease is present. Suitable means include DNA sequencing, northern blotting, southern blotting, Southwestern blotting, probe shift assays (see, e.g., Kumar et al., *AIDS Res. Hum. Retroviruses* 5:345-54 (1989), T4 Endonuclease VII-mediated mismatch-cleavage detection (see, e.g., Youil et al., *Proc. Nat'l. Acad. Sci. USA* 92:87-91 (1995)), Fluorescence Polarization Extension (FPE), Single Strand Length Polymorphism (SSLP), PCR-Restriction Fragment Length Polymorphism (PCR-RFLP), Immobilized Mismatch Binding Protein Mediated (MutS-mediated) Mismatch detection (see, e.g., Wagner et al., *Nucleic Acids Research* 23:3944-48 (1995), reverse dot blotting, (see, e.g., European Patent Application No. 0 511 559), hybridization-mediated enzyme recognition (see, e.g., Kwiatkowski et al., *Mol. Diagn.*, 4(4):353-64 (1999), describing the Invader™ embodiment of this technology by Third-Wave Technologies, Inc.), detection, single-strand conformation polymorphism (SSCP) and gradient denaturing gel electrophoresis to detect probe-target mismatches (e.g., "DGGE", see, e.g., Abrams et al., *Genomics* 7:463-75 (1990), Ganguly et al., *Proc. Nat'l. Acad. Sci. USA* 90:10325-29 (1993), and Myers et al., *Methods Enzymology* 155:501-27 (1987)).

The kit is preferably provided in a microbiologically stable form. Microbiological stability can be achieved by any suitable means, such as by (i) freezing, refrigeration, or lyophilization of kit components, (ii) by heat-, chemical-, or filtration-mediated sterilization or partial sterilization, and/or (iii) by the addition of antimicrobial agents such as azide, detergents, and other suitable reagents to other kit components. The kit can also be optionally provided in a suitable housing that is preferably useful for robotic handling by a clinically-useful sample analyzer. For example, the kit can optionally comprise multiple liquids, each of which are stored in distinct compartments within the housing. In turn, each compartment can be sealed by a device that can be removed, or easily penetrated, by a mechanical device.

The following examples merely illustrate the best mode now contemplated for practicing the invention, but should not be construed to limit the invention. All literature citations herein are expressly incorporated by reference.

Example 1

This example describes the identification of the H101Y missense mutation in the protein kinase C gamma gene and demonstrates that this mutation co-segregates with ataxic neurological disease.

Mapping an Autosomal Dominant Cerebellar Ataxia to Chromosome 19q13.4-Qter:

A four generation family of English and Dutch ethnic background with 14 family members exhibiting unexplained cerebellar ataxia was identified and designated AT08. See Brkanac et al., *Arch. Neurol. Vol.* 59 (August 2002). The family has a relatively uncomplicated form of cerebellar ataxia with mean age of onset of 33 years (range 10 to 50 years) with no evidence for a shortened lifespan and without any differentiating features (such as cognitive decline, visual or other sensory loss, axial myoclonus or peripheral neuropathy). Blood samples were obtained from 24 members in 2 generations of family AT08. DNA was extracted from leukocytes or Epstein-Barr virus-transformed B-lymphoblastoid cell lines as described in Raskind et al., *Am. J. Hum. Genet.* 56:1132-1139 (1995). To identify the locus responsible for the phenotype in this family, a whole genome linkage analysis was performed at the 10 centimorgan (cM) level using the methods as described in Brkanac, Z., et al., *Am. J. Med. Genet.* 114:450-457 (2002). One primer of each pair was end-labeled with gamma 32 phosphorus by a T4 kinase reaction. By haplotype construction, a 22 cM critical region in band 19q13.4 to the q telomere cosegregating with the disease was defined with all the affected individuals found to carry the disease-associated haplotype (see Brkanac et al., *Arch. Neurol. Vol.* 59, 2002)).

Identification of PRKCG Gene Mutations:

Based on sequence data available as of June 2002, a query of the NCBI database disclosed more than 300 genes that mapped to the critical region identified on chromosome 19q (see Brkanac et al., *Arch. Neurol. Vol.* 59, 2002)). PRKCG was identified as a gene that mapped to the critical region on chromosome 19q and was evaluated for DNA sequence alterations in family AT08.

PCR Amplification of Exons 1-18:

DNA was isolated from peripheral blood and each of the 18 exons of the PRKCG gene were PCR-amplified from subject genomic DNA utilizing primer pairs listed in TABLE 1 and TABLE 2. PCR reactions were carried out in 20 µl containing 1×PCR buffer of 10 mM Tris-HCL (pH 8.3 at 25° C.), 50 mM KCL, 1.5 mM $MgCl^2$, 0.001% (w/v) gelatin at final concentration, 10 pmol of each forward and reverse primer, 200 µM dNTP (Sigma, St. Louis, Mo.), and 1.0 U JumpStart Taq DNA Polymerase (Sigma, St. Louis, Mo.). The PCR amplification protocol included an initial denaturation at 95° C. for 5 min., 34 cycles of 94° C. for 30 sec., 60° C. (or 56° C. for some fragments listed in TABLE 2) for 45 sec. and 72° C. for 90 sec., followed by a final extension at 72° C. for 10 min. 5 µl of PCR product was characterized by gel electrophoresis/ethidium bromide staining for the presence of a single correctly sized band.

Direct DNA Sequencing of the PCR Fragments:

5 µl of PCR product from each sample confirmed to have a single correctly sized band was treated with 1 µl of ExoSAP-IT (US Biochemical, Cleveland, Ohio) at 37° C. for 2 hours followed by heat inactivation at 85° C. for 10 minutes. Direct DNA sequencing of the purified fragments was carried out by using a BigDye Terminator Cycle Sequencing Ready Reaction Kit (Applied Biosystems Inc., Foster City, Calif.). The primers used for sequencing are listed in TABLE 2. For initial mutation screening, either forward or reverse primer was used. The PCR reaction contained 3 µl of treated PCR product (~100 ng), 3 pmol primer, 1 µl sequencing buffer and 2 µl of BigDye reagent in a total volume of 10 µl. The sequencing reaction was carried out in a PTC-100 Programmable Thermal Controller (MJ Research Inc., Waltham, Mass.) with cycle conditions of 96° C. for 2 min., 30 cycles of 96° C. for 15 sec., 50° C. for 10 sec. and 60° C. for 4 min. The sequencing product was purified by ethanol/EDTA precipitation, then electrophoresed on an ABI DNA Sequencer (Applied Biosystems Inc., Foster City, Calif.).

Evaluation of Cosegregation of Ataxia and Genetic Mutations:

Radioisotope dideoxy sequencing using two bases (wild type C and mutant T) was performed to evaluate the cosegregation of ataxia and the mutations in AT08 and to screen normal controls for a possible polymorphism. The forward primer for exon 4 was end-labeled with $[\gamma^{32}]P$ by the T4 kinase reaction and sequencing was performed with the AmpliCycle Sequencing Kit (Applied Biosytems Inc.). The sequencing products were then electrophoresed at 50° C. on 6% polyacrylamide gels containing 7M urea.

Results:

The C to T Transition in Nucleotide 301 (H101Y)

A C to T transition in nucleotide 301, (as counted from the cDNA start codon as shown in SEQ ID NO:1) was detected in exon 4, which predicts substitution of hydrophilic tyrosine for hydrophobic histidine at amino acid position 101 (H101Y). The mutation was found in 10 members of the family and segregated with ataxia in all ten cases. Of the group that is currently unaffected but at risk (twenty and younger), two individuals inherited the C to T mutation, and 13 individuals had the wild-type sequence. The C to T nucleotide change was not found in 192 normal controls (384 chromosomes). The 101 histidine residue in the Cys2 region is evolutionarily conserved in all mammals and invertebrates studied and in all Cys2 regions in the PRKCG family.

Example 2

This example describes the identification of the S119P and G128D missense mutations in the protein kinase C gamma gene.

Subjects Tested:

Forty ataxia subjects were screened for mutations in the PRKCG gene. Twenty-seven of the subjects had positive family histories of ataxia, and twelve were sporadic cases. All forty subjects had previously tested negative for expansions in the genes for SCA1, SCA2, SCA3 and SCA6. Twenty-seven subjects had also tested negative for abnormal alleles of SCAT and SCA8. Ninety-six control samples (192 chromosomes) were tested in this study.

Methods:

The entire coding region of PRKCG was sequenced in genomic DNA by first PCR amplifying the 18 exons and sequencing each using the primers shown in TABLE 2 as described in Example 1.

Results:

T to C Transition in Nucleotide 355 (S119P):

A T to C transition in nucleotide 355, predicting a hydrophilic serine to hydrophobic proline substitution at residue 119 (S119P) was found in an affected woman and her affected son and affected daughter (mean age of onset at 42 years, range 35 to 51 years; family AT29). Serine residue 119 is conserved in all mammalian cys2 regions and most PRKCG family members.

G to A Transition in Nucleotide 383 (G128D):

A G to A transition in nucleotide 383 predicting a glycine to aspartate substitution at residue 128 (G128D) was found in a 55-year-old man (with onset of ataxia in his early twenties), with no family history of ataxia (family AT117). Glycine residue 128 is conserved in all mammalian cys2 regions and most PRKCG family members.

RFLP analysis was also performed on samples from subjects exhibiting ataxia containing the G128D mutation a panel of 96 normal control individuals. MwoI digestion of the 260 bp exon 4 fragment from ataxia samples resulted in the pattern shown in TABLE 4 for mutant-type samples. Of the 96 normal control samples, all MwoI restriction patterns corresponded to the expected fragment pattern for wild type shown in TABLE 4.

TABLE 4

THE CONDITIONS OF RFLP ANALYSIS FOR SCREEN IDENTIFIED MUTATIONS IN PRKCG GENE

| | | | Restriction Fragment Sizes (bp) | | Conditions | |
| --- | --- | --- | --- | --- | --- | --- |
| Mutation | Primer Set | Enzyme | Wild-type | Mutant-type | Temp | Buffer(s) |
| 207C to T (C69C) | 3F (SEQ ID NO: 8), 3R (SEQ ID NO: 9) | PstI | 95, 156 | 251 | 37° C. | NEBuffer 3 + BSA |
| 204C to G (V68V) | 3F (SEQ ID NO: 8), 3R (SEQ ID NO: 9) | BsgI | 251 | 96, 155 | 37° C. | NEBuffer 4 + SAM |
| 355T to C (S119P) | 4F (SEQ ID NO: 10), 4R (SEQ ID NO: 11) | HaeIII | 11, 25, 36, 188 | 11, 25, 36, 58, 130 | 37° C. | NEBuffer 2 |
| 383G to A (G128D) | 4F (SEQ ID NO: 10), 4R (SEQ ID NO: 11) | MwoI | 55, 59, 72, 74 | 55, 59, 146 | 60° C. | NEBuffer MwoI |
| 1081A to G (S361G) | 10F (SEQ ID NO: 20), 10R (SEQ ID NO: 21) | AciI | 6, 71, 200 | 6, 66, 71, 134 | 37° C. | NEBuffer 3 |
| 1683G to A (E561E) | 16F (SEQ ID NO: 30), 16R (SEQ ID NO: 31) | SapI | 420 | 174, 276 | 37° C. | NEBuffer 4 |
| 1789C to A (R597S) | 17F (SEQ ID NO: 32), 17R (SEQ ID NO: 33) | HaeII | 94, 176 | 270 | 37° C. | NEBuffer 4 + BSA |

Controls:

Of the ninety-six control samples (192 chromosomes) that were tested in this study, none exhibited either of these two single nucleotide changes.

Example 3

This example describes the use of restriction fragment length polymorphism (RFLP) analysis to identify mutations in the PRKCG gene.

Restriction Fragment Length Polymorphism (RFLP) Analysis:

Several of the identified mutations, including C69C, V68V, S119P, G128D, S361G, E561E and R597S, alter the restriction endonuclease digestion pattern of specific restriction endonucleases as shown in TABLE 4. The first column of TABLE 4 describes the mutations amenable to RFLP analysis, the second column provides a useful primer set for amplification of the region encompassing the mutation, the third column provides the relevant restriction endonuclease for use in digestion of the PCR fragment, the fourth and fifth columns provide the expected restriction enzyme digested fragments for wild-type, and mutant genes respectively. The final two columns provide the reaction conditions appropriate for each restriction enzyme digestion listed.

Results:

RFLP analysis was performed on samples from subjects exhibiting ataxia containing the S119P mutation and a panel of 96 normal control individuals. HaeIII digestion of the 260 bp exon 4 fragment from ataxia samples resulted in the pattern shown in TABLE 4 for mutant-type samples. Of the 96 normal control samples, all HaeIII restriction patterns corresponded to the expected fragment pattern for wild type shown in TABLE 4.

Example 4

This example describes a kit and method of use for identifying genetic mutations associated with ataxic neurological disease in a mammalian subject, and for determining susceptibility or presence of ataxic neurological disease in a test subject. Additional mutants R41P, S361G and R597S have been identified through the use of this kit and method.

Methods Utilized:

PCR Amplification:

Carried out as described in Example 1

Direct Sequencing:

Carried out as described in Example 1

Data Analysis:

The resulting sequences were aligned with the known exon sequence using a multiple sequence alignment tool, Sequencher (Gene Codes Corporation, Ann Arbor, Mich.), in order to identify any nucleotide changes. Electropherograms were also visually examined to detect heterozygous base changes that might have been missed by Sequencher.

Confirmation of the Nucleotide Changes:

Once a nucleotide change was detected, the exon fragment encompassing the suspected mutation was subjected to PCR amplification and direct sequencing again, using both forward and reverse primers.

For familial cases, when the nucleotide change is confirmed, with consent, the available family members, including affected and at risk unaffected individuals, are tested to confirm that the mutation segregates with the disease. After appropriate consent for clinical testing is obtained, the test may also be used for presymptomatic diagnosis in at-risk individuals.

Contents of the PRKCG Mutation Kit:

1. 10×PCR buffer (100 mM Tris-HCl (pH 8.3 at 25° C.), 500 mM KCl, 15 mM $MgCl_2$, 0.01% (w/v) gelatin 2. dNTP mix: dATP, dCTP, dGTP, dTTP at 10 mM each (Sigma, St. Louis, Mo.)
3. JumpStart Taq DNA polymerase (Sigma, St. Louis, Mo.)
4. Primers for amplification of each PRKCG exon and the adjacent intronic sequences at 10 µM each (as shown in TABLE 1 and TABLE 2)
5. Exo-SAP-IT (US Biochemical, Cleveland, Ohio)
6. BigDye Terminator Cycle Sequencing Ready Reaction Kit (Applied Biosystems Inc., Foster City, Calif.)

Results:
A total of 160 individuals exhibiting ataxia were screened for mutations and the R41P, S361G and R597S mutations were found once each.

A G to C transition was discovered in nucleotide 122 predicting a R to P substitution at residue 41 in exon 1. An A to G transition was discovered in nucleotide 380 predicting a Q to R substitution at residue 127 in exon 4. An A to G transition was discovered in nucleotide 1081, predicting an S to G substitution at residue 361 in exon 10, and a C to A transition was discovered in nucleotide 1789 predicting an R to S substitution at residue 597 in exon 17.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A kit for determining susceptibility or presence of ataxic neurological disease in a human subject based on the detection of a mutation in a human protein kinase C gamma (PRKCG) gene comprising:
   (i) one or more nucleic acid primer molecule pairs, wherein each primer molecule is identical to at least 18 contiguous nucleotides occurring in a PRKCG nucleic acid sequence as set forth in SEQ ID NO:3 or the complement thereof, wherein the one or more nucleic acid primer molecule pairs permit amplification of a portion of the PRKCG nucleic acid sequence comprising any of: nucleotides 440 to 609 of SEQ ID NO:3 (exon 1), nucleotides 2106 to 2188 of SEQ ID NO:3 (exon 3), nucleotides 7583 to 7694 of SEQ ID NO:3 (exon 4), and nucleotides 15904 to 16056 of SEQ ID NO:3 (exon 10);
   (ii) one or more nucleic acid probes that hybridize to a PRKCG nucleic acid sequence encoding a mutation selected from the group consisting of: H101Y, S119P, Q127R, G128D, S361G, and a deletion of amino acid H101, and wherein each of said one or more nucleic acid probes comprises a sequence complementary to the mutation of the PRKCG nucleic acid sequence;
   (iii) written indicia indicating a correlation between the presence of said mutation and risk of ataxic neurological disease; and
   (iv) amplification reaction reagents suitable for use in nucleic acid amplification,
   wherein each of said one or more nucleic acid probes is linked to a fluorescent molecule.

2. The kit of claim 1, further comprising nucleic acid primer molecules for sequencing across an amplified portion of a protein kinase C gamma gene.

3. The kit of claim 1, further comprising control DNA.

4. The kit of claim 1, wherein said mutation encodes H101Y and wherein said primers comprise SEQ ID NO:10 and SEQ ID NO:11.

5. The kit of claim 1, wherein said mutation encodes S119P and wherein said primers comprise SEQ ID NO:10 and SEQ ID NO:11.

6. The kit of claim 1, wherein said mutation encodes Q127R and wherein said primers comprise SEQ ID NO:10 and SEQ ID NO:11.

7. The kit of claim 1, wherein said mutation encodes G128D and wherein said primers comprise SEQ ID NO:10 and SEQ ID NO:11.

8. The kit of claim 1, wherein said mutation encodes S361G and wherein said primers comprise SEQ ID NO:20 and SEQ ID NO:21.

9. The kit of claim 1, wherein said mutation comprises a deletion of amino acid H101 and wherein said primers comprise SEQ ID NO:10 and SEQ ID NO:13.

10. The kit of claim 1, wherein the kit comprises one or more nucleic acid primer molecules which hybridize to an intron sequence adjacent to at least one exon selected from the group consisting of: exon 1 (nucleotides 440 to 609 of SEQ ID NO:3); exon 3 (nucleotides 2106 to 2188 of SEQ ID NO:3); exon 4 (nucleotides 7583 to 7694 of SEQ ID NO:3); and exon 10 (nucleotides 15904 to 16056 of SEQ ID NO:3).

11. The kit of claim 1, wherein the kit comprises one or more nucleic acid primer molecules which hybridize to a nucleic acid sequence encoding an amino acid residue selected from the group consisting of amino acid residues 41, 101, 119, 127, 128, and 361 of SEQ ID NO:2.

12. The kit of claim 11, wherein the kit comprises one or more nucleic acid primer molecules which hybridize to a nucleic acid sequence encoding a mutant amino acid residue selected from the group consisting of R41P, H101Y, S119P, Q127R, G128D, S361G, and a deletion of 101H of SEQ ID NO:2.

\* \* \* \* \*

SEQUENCE LISTING

```
<160> NUMBER OF SEQ ID NOS: 35

<210> SEQ ID NO 1
<211> LENGTH: 2910
<212> TYPE: DNA
<213> ORGANISM: Homo Sapien
<220> FEATURE:
<221> NAME/KEY: CDS
<222> LOCATION: (1)..(2091)

<400> SEQUENCE: 1 atg gct ggt ctg ggc ccc ggc gta ggc gat tca gag ggg gga ccc cgg      48
Met Ala Gly Leu Gly Pro Gly Val Gly Asp Ser Glu Gly Gly Pro Arg
1               5                   10                  15 ccc ctg ttt tgc aga aag ggg gcc ctg agg cag aag gtg gtc cac gaa      96
Pro Leu Phe Cys Arg Lys Gly Ala Leu Arg Gln Lys Val Val His Glu
            20                  25                  30 gtc aag agc cac aag ttc acc gct cgc ttc ttc aag cag ccc acc ttc     144
Val Lys Ser His Lys Phe Thr Ala Arg Phe Phe Lys Gln Pro Thr Phe
        35                  40                  45 tgc agc cac tgc acc gac ttc atc tgg ggt atc gga aag cag ggc ctg     192
Cys Ser His Cys Thr Asp Phe Ile Trp Gly Ile Gly Lys Gln Gly Leu
    50                  55                  60 caa tgt caa gtc tgc agc ttt gtg gtt cat cga cga tgc cac gaa ttt     240
Gln Cys Gln Val Cys Ser Phe Val Val His Arg Arg Cys His Glu Phe
65                  70                  75                  80 gtg acc ttc gag tgt cca ggc gct ggg aag ggc ccc cag acg gat gac     288
Val Thr Phe Glu Cys Pro Gly Ala Gly Lys Gly Pro Gln Thr Asp Asp
                85                  90                  95 ccc cgg aac aaa cac aag ttc cgc ctg cat agc tac agc agc ccc acc     336
Pro Arg Asn Lys His Lys Phe Arg Leu His Ser Tyr Ser Ser Pro Thr
            100                 105                 110 ttc tgc gac cac tgt ggc tcc ctc ctc tac ggg ctt gtg cac cag ggc     384
Phe Cys Asp His Cys Gly Ser Leu Leu Tyr Gly Leu Val His Gln Gly
        115                 120                 125 atg aaa tgc tcc tgc tgc gag atg aac gtg cac cgg cgc tgt gtg cgt     432
Met Lys Cys Ser Cys Cys Glu Met Asn Val His Arg Arg Cys Val Arg
    130                 135                 140 agc gtg ccc tcc ctg tgc ggt gtg gac cac acc gag cgc cgc ggg cgc     480
Ser Val Pro Ser Leu Cys Gly Val Asp His Thr Glu Arg Arg Gly Arg
145                 150                 155                 160 ctg cag ctg gag atc cgg gct ccc aca gca gat gag atc cac gta act     528
Leu Gln Leu Glu Ile Arg Ala Pro Thr Ala Asp Glu Ile His Val Thr
                165                 170                 175 gtt ggc gag gcc cgt aac cta att cct atg gac ccc aat ggt ctc tct     576
Val Gly Glu Ala Arg Asn Leu Ile Pro Met Asp Pro Asn Gly Leu Ser
            180                 185                 190
```

```
gat ccc tat gtg aaa ctg aag ctc atc cca gac cct cgg aac ctg acg      624
Asp Pro Tyr Val Lys Leu Lys Leu Ile Pro Asp Pro Arg Asn Leu Thr
        195                 200                 205 aaa cag aag acc cga acg gtg aaa gcc acg cta aac cct gtg tgg aat      672
Lys Gln Lys Thr Arg Thr Val Lys Ala Thr Leu Asn Pro Val Trp Asn
210                 215                 220 gag acc ttt gtg ttc aac ctg aag cca gga gat gtg gag cgc cgg ctc      720
Glu Thr Phe Val Phe Asn Leu Lys Pro Gly Asp Val Glu Arg Arg Leu
225                 230                 235                 240 agc gtg gag gtg tgg gac tgg gac cgg acc tcc cgc aac gac ttc atg      768
Ser Val Glu Val Trp Asp Trp Asp Arg Thr Ser Arg Asn Asp Phe Met
                245                 250                 255 ggg gcc atg tcc ttt ggc gtc tcg gag ctg ctc aag gcg ccc gtg gat      816
Gly Ala Met Ser Phe Gly Val Ser Glu Leu Leu Lys Ala Pro Val Asp
                260                 265                 270 ggc tgg tac aag tta ctg aac cag gag gag ggc gag tat tac aat gtg      864
Gly Trp Tyr Lys Leu Leu Asn Gln Glu Glu Gly Glu Tyr Tyr Asn Val
            275                 280                 285 ccg gtg gcc gat gct gac aac tgc agc ctc ctc cag aag ttt gag gct      912
Pro Val Ala Asp Ala Asp Asn Cys Ser Leu Leu Gln Lys Phe Glu Ala
290                 295                 300 tgt aac tac ccc ctg gaa ttg tat gag cgg gtg cgg atg ggc ccc tct      960
Cys Asn Tyr Pro Leu Glu Leu Tyr Glu Arg Val Arg Met Gly Pro Ser
305                 310                 315                 320 tcc tct ccc atc ccc tcc cct tcc cct agt ccc acc gac ccc aag cgc     1008
Ser Ser Pro Ile Pro Ser Pro Ser Pro Ser Pro Thr Asp Pro Lys Arg
                325                 330                 335 tgc ttc ttc ggg gcg agt cca gga cgc ctg cac atc tcc gac ttc agc     1056
Cys Phe Phe Gly Ala Ser Pro Gly Arg Leu His Ile Ser Asp Phe Ser
                340                 345                 350 ttc ctc atg gtt cta gga aaa ggc agt ttt ggg aag gtg atg ctg gcc     1104
Phe Leu Met Val Leu Gly Lys Gly Ser Phe Gly Lys Val Met Leu Ala
            355                 360                 365 gag cgc agg ggc tct gat gag ctc tac gcc atc aag atc ttg aaa aag     1152
Glu Arg Arg Gly Ser Asp Glu Leu Tyr Ala Ile Lys Ile Leu Lys Lys
370                 375                 380 gac gtg atc gtc cag gac gac gat gtg gac tgc acg ctg gtg gag aaa     1200
Asp Val Ile Val Gln Asp Asp Asp Val Asp Cys Thr Leu Val Glu Lys
385                 390                 395                 400 cgt gtg ctg gcg ctg ggg ggc cgg ggt cct ggc ggc cgg ccc cac ttc     1248
Arg Val Leu Ala Leu Gly Gly Arg Gly Pro Gly Gly Arg Pro His Phe
                405                 410                 415 ctc acc cag ctc cac tcc acc ttc cag acc ccg gac cgc ctg tat ttc     1296
Leu Thr Gln Leu His Ser Thr Phe Gln Thr Pro Asp Arg Leu Tyr Phe
                420                 425                 430 gtg atg gag tac gtc acc ggg gga gac ttg atg tac cac att caa cag     1344
Val Met Glu Tyr Val Thr Gly Gly Asp Leu Met Tyr His Ile Gln Gln
            435                 440                 445 ctg ggc aag ttt aag gag ccc cat gca gcg ttc tac gcg gca gaa atc     1392
Leu Gly Lys Phe Lys Glu Pro His Ala Ala Phe Tyr Ala Ala Glu Ile
450                 455                 460 gct atc ggc ctc ttc ttc ctt cac aat cag ggc atc atc tac agg gac     1440
Ala Ile Gly Leu Phe Phe Leu His Asn Gln Gly Ile Ile Tyr Arg Asp
465                 470                 475                 480 ctg aag ctg gac aat gtg atg ctg gat gct gag gga cac atc aag atc     1488
Leu Lys Leu Asp Asn Val Met Leu Asp Ala Glu Gly His Ile Lys Ile
                485                 490                 495 act gac ttt ggc atg tgt aag gag aac gtc ttc ccc ggg acg aca acc     1536
Thr Asp Phe Gly Met Cys Lys Glu Asn Val Phe Pro Gly Thr Thr Thr
                500                 505                 510
```

```
cgc acc ttc tgc ggg acc ccg gac tac ata gcc ccg gag atc att gcc   1584
Arg Thr Phe Cys Gly Thr Pro Asp Tyr Ile Ala Pro Glu Ile Ile Ala
        515                 520                 525 tac cag ccc tat ggg aag tct gtc gat tgg tgg tcc ttt gga gtt ctg   1632
Tyr Gln Pro Tyr Gly Lys Ser Val Asp Trp Trp Ser Phe Gly Val Leu
        530                 535                 540 ctg tat gag atg ttg gca gga cag cct ccc ttc gat ggg gag gac gag   1680
Leu Tyr Glu Met Leu Ala Gly Gln Pro Pro Phe Asp Gly Glu Asp Glu
545                 550                 555                 560 gag gag ctg ttt cag gcc atc atg gaa caa act gtc acc tac ccc aag   1728
Glu Glu Leu Phe Gln Ala Ile Met Glu Gln Thr Val Thr Tyr Pro Lys
                565                 570                 575 tcg ctt tcc cgg gaa gcc gtg gcc atc tgc aag ggg ttc ctg acc aag   1776
Ser Leu Ser Arg Glu Ala Val Ala Ile Cys Lys Gly Phe Leu Thr Lys
            580                 585                 590 cac cca ggg aag cgc ctg ggc tca ggg cct gat ggg gaa cct acc atc   1824
His Pro Gly Lys Arg Leu Gly Ser Gly Pro Asp Gly Glu Pro Thr Ile
        595                 600                 605 cgt gca cat ggc ttt ttc cgc tgg att gac tgg gag cgg ctg gaa cga   1872
Arg Ala His Gly Phe Phe Arg Trp Ile Asp Trp Glu Arg Leu Glu Arg
    610                 615                 620 ttg gag atc ccg cct cct ttc aga ccc cgc ccg tgt ggc cgc agc ggc   1920
Leu Glu Ile Pro Pro Pro Phe Arg Pro Arg Pro Cys Gly Arg Ser Gly
625                 630                 635                 640 gag aac ttt gac aag ttc ttc acg cgg gcg gcg cca gcg ctg acc cct   1968
Glu Asn Phe Asp Lys Phe Phe Thr Arg Ala Ala Pro Ala Leu Thr Pro
                645                 650                 655 cca gac cgc cta gtc ctg gcc agc atc gac cag gcc gat ttc cag ggc   2016
Pro Asp Arg Leu Val Leu Ala Ser Ile Asp Gln Ala Asp Phe Gln Gly
            660                 665                 670 ttc acc tac gtg aac ccc gac ttc gtg cac ccg gat gcc cgc agc ccc   2064
Phe Thr Tyr Val Asn Pro Asp Phe Val His Pro Asp Ala Arg Ser Pro
        675                 680                 685 acc agc cca gtg cct gtg ccc gtc atg taatctcacc cgccgccact         2111
Thr Ser Pro Val Pro Val Pro Val Met
        690                 695 aggtgtcccc aacgtcccct ccgccgtgcc ggcggcagcc ccacttcacc cccaacttca   2171
ccaccccctg tcccattcta gatcctgcac cccagcattc cagctctgcc cccgcgggtt   2231
ctagacgccc ctcccaagcg ttcctggcct tctgaactcc atacagcctc tacagccgtc   2291
ccgcgttcaa gacttgagcg gagcccgata ttctccctga ccttagcgtt ctggactctg   2351
ccccaatcgg gtccagagac cacaccacta accatcccca actccatggg gttcgagact   2411
ccatcttggt agttctgtgc ctcccccag accccgcccc tggggaaata gcctcacggg   2471
gttggctgtt ccagactcag gttccagaac agccctcggc ctccgaggct cccgcctcc   2531 actctagttc tagatgagtg ggaggcgtgc cccctcctc cagtacgtcc cgctgctgtg   2591
ctctggggat ttctgggata tatggaggat tctttcccca gaggctccca atcagctttt   2651
gttctagact tccccatccc gaagccatca cttctccccg cagcccgcct gccgtgcatg   2711
gctcctgtct ggctcggacc cacccccaact ctcccagtg cctgccactc tctgggactc   2771
tcctcctccc ctcctcttcc cttagcctct cccaccggc cacagctgct ggagaataaa   2831
tttgggatgc tgatgaaaaa aaaaaaaaa aaaaaaaa aaaaaaaa aaaaaaaa        2891 aaaaaaaaaa aaaaaaaaa                                               2910

<210> SEQ ID NO 2
```

```
<211> LENGTH: 697
<212> TYPE: PRT
<213> ORGANISM: Homo Sapien

<400> SEQUENCE: 2
```

| | | | | | | | | | | | | | | |
|---|---|---|---|---|---|---|---|---|---|---|---|---|---|---|
|Met|Ala|Gly|Leu|Gly|Pro|Gly|Val|Gly|Asp|Ser|Glu|Gly|Gly|Pro|Arg
1| | | |5| | | | |10| | | | |15|

Pro Leu Phe Cys Arg Lys Gly Ala Leu Arg Gln Lys Val Val His Glu
            20                  25                  30

Val Lys Ser His Lys Phe Thr Ala Arg Phe Phe Lys Gln Pro Thr Phe
        35                  40                  45

Cys Ser His Cys Thr Asp Phe Ile Trp Gly Ile Gly Lys Gln Gly Leu
    50                  55                  60

Gln Cys Gln Val Cys Ser Phe Val Val His Arg Arg Cys His Glu Phe
65                  70                  75                  80

Val Thr Phe Glu Cys Pro Gly Ala Gly Lys Gly Pro Gln Thr Asp Asp
                85                  90                  95

Pro Arg Asn Lys His Lys Phe Arg Leu His Ser Tyr Ser Ser Pro Thr
            100                 105                 110

Phe Cys Asp His Cys Gly Ser Leu Leu Tyr Gly Leu Val His Gln Gly
        115                 120                 125

Met Lys Cys Ser Cys Cys Glu Met Asn Val His Arg Arg Cys Val Arg
    130                 135                 140

Ser Val Pro Ser Leu Cys Gly Val Asp His Thr Glu Arg Arg Gly Arg
145                 150                 155                 160

Leu Gln Leu Glu Ile Arg Ala Pro Thr Ala Asp Glu Ile His Val Thr
                165                 170                 175

Val Gly Glu Ala Arg Asn Leu Ile Pro Met Asp Pro Asn Gly Leu Ser
            180                 185                 190

Asp Pro Tyr Val Lys Leu Lys Leu Ile Pro Asp Pro Arg Asn Leu Thr
        195                 200                 205

Lys Gln Lys Thr Arg Thr Val Lys Ala Thr Leu Asn Pro Val Trp Asn
    210                 215                 220

Glu Thr Phe Val Phe Asn Leu Lys Pro Gly Asp Val Glu Arg Arg Leu
225                 230                 235                 240

Ser Val Glu Val Trp Asp Trp Asp Arg Thr Ser Arg Asn Asp Phe Met
                245                 250                 255

Gly Ala Met Ser Phe Gly Val Ser Glu Leu Leu Lys Ala Pro Val Asp
            260                 265                 270

Gly Trp Tyr Lys Leu Leu Asn Gln Glu Glu Gly Glu Tyr Tyr Asn Val
        275                 280                 285

Pro Val Ala Asp Ala Asp Asn Cys Ser Leu Leu Gln Lys Phe Glu Ala
    290                 295                 300

Cys Asn Tyr Pro Leu Glu Leu Tyr Glu Arg Val Arg Met Gly Pro Ser
305                 310                 315                 320

Ser Ser Pro Ile Pro Ser Pro Ser Pro Ser Thr Asp Pro Lys Arg
                325                 330                 335

Cys Phe Phe Gly Ala Ser Pro Gly Arg Leu His Ile Ser Asp Phe Ser
            340                 345                 350

Phe Leu Met Val Leu Gly Lys Gly Ser Phe Gly Lys Val Met Leu Ala
        355                 360                 365

Glu Arg Arg Gly Ser Asp Glu Leu Tyr Ala Ile Lys Ile Leu Lys Lys
    370                 375                 380

Asp Val Ile Val Gln Asp Asp Asp Val Asp Cys Thr Leu Val Glu Lys

```
                385                 390                 395                 400
        Arg Val Leu Ala Leu Gly Gly Arg Gly Pro Gly Gly Arg Pro His Phe
                            405                 410                 415
        Leu Thr Gln Leu His Ser Thr Phe Gln Thr Pro Asp Arg Leu Tyr Phe
                            420                 425                 430
        Val Met Glu Tyr Val Thr Gly Gly Asp Leu Met Tyr His Ile Gln Gln
                            435                 440                 445
        Leu Gly Lys Phe Lys Glu Pro His Ala Ala Phe Tyr Ala Ala Glu Ile
                            450                 455                 460
        Ala Ile Gly Leu Phe Phe Leu His Asn Gln Gly Ile Ile Tyr Arg Asp
            465                 470                 475                 480
        Leu Lys Leu Asp Asn Val Met Leu Asp Ala Glu Gly His Ile Lys Ile
                            485                 490                 495
        Thr Asp Phe Gly Met Cys Lys Glu Asn Val Phe Pro Gly Thr Thr Thr
                            500                 505                 510
        Arg Thr Phe Cys Gly Thr Pro Asp Tyr Ile Ala Pro Glu Ile Ile Ala
                            515                 520                 525
        Tyr Gln Pro Tyr Gly Lys Ser Val Asp Trp Trp Ser Phe Gly Val Leu
                            530                 535                 540
        Leu Tyr Glu Met Leu Ala Gly Gln Pro Pro Phe Asp Gly Glu Asp Glu
        545                 550                 555                 560
        Glu Glu Leu Phe Gln Ala Ile Met Glu Gln Thr Val Thr Tyr Pro Lys
                            565                 570                 575
        Ser Leu Ser Arg Glu Ala Val Ala Ile Cys Lys Gly Phe Leu Thr Lys
                            580                 585                 590
        His Pro Gly Lys Arg Leu Gly Ser Gly Pro Asp Gly Glu Pro Thr Ile
                            595                 600                 605
        Arg Ala His Gly Phe Phe Arg Trp Ile Asp Trp Glu Arg Leu Glu Arg
                            610                 615                 620
        Leu Glu Ile Pro Pro Pro Phe Arg Pro Arg Pro Cys Gly Arg Ser Gly
        625                 630                 635                 640
        Glu Asn Phe Asp Lys Phe Phe Thr Arg Ala Ala Pro Ala Leu Thr Pro
                            645                 650                 655
        Pro Asp Arg Leu Val Leu Ala Ser Ile Asp Gln Ala Asp Phe Gln Gly
                            660                 665                 670
        Phe Thr Tyr Val Asn Pro Asp Phe Val His Pro Asp Ala Arg Ser Pro
                            675                 680                 685
        Thr Ser Pro Val Pro Val Pro Val Met
                            690                 695

<210> SEQ ID NO 3
<211> LENGTH: 25301
<212> TYPE: DNA
<213> ORGANISM: Homo Sapien

<400> SEQUENCE: 3
agcccccgga gtgggtgtgt gcacgtgtgg ggggcgggga gggaggacat ttgtcccgtg      60
tctccgggag gggagcgcct ttaagccgaa acccgccct  ctcggtcgtc ctggcaacgc     120 ctccccccaac ccggggctcc cacatttcag caggtgccgg agctggagct cccaccgccg    180
ccgcccgtgc ctccggctgc cggcgcccct gcctttggct cttcctcccc actcgcccgc    240
tccccctggc ggagccggcg cgcccggggt gccgctccct gcctggcgcg ctccgcacct    300
ggaggtgcct tgcccctctc ctgcccacct cggaatttcc ctgtggctcc tttgatcctt    360
```

```
cgagtctcca gctcctctcc cttccacctg tttcccccaa gaaaggcagg atcctggtcc      420
ctgctacgtt tctggggcca tggctggtct gggccccggc gtaggcgatt cagagggggg      480
accccggccc ctgttttgca gaaagggggc cctgaggcag aaggtggtcc acgaagtcaa      540
gagccacaag ttcaccgctc gcttcttcaa gcagcccacc ttctgcagcc actgcaccga      600
cttcatctgg tgagggaagg gggctggggg actggggac gagggacta ggggtgcaga       660 ctcctatcac gccgacccct gtggaaggaa aaggagggg gctgtagtcc cgactcccag       720
gttctaggat ggccagggaa cgctgggagc ttcgactcct gggtttcagt gaggaggagg      780
ctggttcctg gagtgctggg tccgaggag gaggaggctg gaggacagag gtcctggagt       840
cttgggtctg agggaggaag ggcctggggg gctgggagcc tggattcctg ggtctgaagg      900
aggaagaaac tgggggctga actccagtct aagggaagaa gggctggggg ccaaaatttc      960
tgggttctag aaagaggagg tggccggggc ttggacacct gggccctgcg ggaggagggt     1020
cagagagcgc aggcccctg tggctcgcag aggttggggg tccaggtacc cctttctgca     1080
ctgacctagg atccctgact cttccagggg tatcggaaag cagggcctgc aatgtcaagg     1140
taagagctgg ggaccggggc tcctgggacc ctcaggaggg tggaggctgg gccccacag      1200 ctgaggctgc ttgacacacg tgttctctgg tccccagaga ggcgcggggg agcccggggc     1260 gggggggtgtg gcagagacac agcctgtggt ggggagggag cttttgatggt ggggccaccg    1320 cggaggtggt gctgggggcc cctccctcgg ccggctccag gtggggacag atatttggag     1380
aatctgttgc catgggaaca tggagatttg aaaaggggga gctgaagggg ggaaggggga    1440
gggggctgga gatgcaaagt cagagccccc ccccaccca ggctgccgtc gccatgacaa      1500
caccagccgt cctaggcagg ggcaggccgg gtggggtcac caatgggcga gtgggggccg      1560
ggcggggccg gcagttctgg ggggcgggag aggggggcga gtccttgagc accagctgct     1620
actgctgaga acagagtgag tcagggtggg gggcgggccg gcagcagcgc ccccagactc     1680
acttctgccc aagttgctgc ttcctgggct gcgtctgaag atatttcggt tttcgctctt     1740
tgaatctgtc tgcctctctc ctggctttct gatctccgtc cgtgggcctg tgtctgtttg     1800
tcaatgggat cctatttct ttctctcttt ttccatctcc cttccctgag ctctgtgctc     1860
tgtgtctctc tgtaagtctc tgcgtctctg tttctgactc tgagcccatc tcttgggttt     1920
ctgtctcctg cttctctctc tggcctccga ttttctctct gttggactct ctgtgttgag     1980
atccctctct ttctggtttt ctcagtgtcc gagttccgct ctctcttccc aattttctgt     2040
ctgctggggt ctcccgctgg actaatccat gcctccgtct gtgtctctat gattttcatc     2100
tatagtctgc agctttgtgg ttcatcgacg atgccacgaa tttgtgacct tcgagtgtcc     2160
aggcgctggg aagggccccc agacggacgt gagtgctcgg acacctggtt ctcctcctcg     2220
ggccgtgccc ccgccctcac cccctcggcg tccgtcccaa tttctcctgc tatttttatg     2280
gctgggaggg gagggggct ggagagatag ggggagctat ctggcccaga ttccttgccc      2340
ttggcctgga aaggggaat gcgaggggga ctgacaggct ggggacacgg gtggggcaca      2400
gagaggaggc cggggtgagg agactgaaga tgggtgctgc cgggggtggg ctgtgatcca     2460
ggggtgaagg gatttaaaaa ttgagagctg aggggcacac ggagaaaat atcagtgcag      2520 gtgcggagat gccaacataa gacagaggga atctcaggga gaggaacaga gacagaagaa     2580
gacagagacc taggagagac tgaagctgag gcagagagag agagagatgg agcagagaaa     2640
gaaccaggga gaaagagagg aatttggagg caccaaaaga tggacagaga aactccaaga     2700
gacggagaca cagacacctg gagaaagaga ctaaaataga aaatggtgga tacagacaac     2760
```

```
agcttaggag atgctgagag gagacccagg gaagtcccac agtacacttg cacacatgtg   2820
cgtgcatgta cagatgcccc tgtcatcaca gatgtgcagc acgcagagac acacagcctc   2880
tccccacccc ctctctctcc atcagaggct cacaagacca gtcaaccctg agtgcccatt   2940
cccgttccct tttctgcttt atctctgagc ctcagtttcc tcctctataa aatggggctg   3000
atgatctagc attgaccaac agaactgttt acagtgacgg aagcattctg tacatgcact   3060
gtccaatagg cagccaccag ctccatgtag ccagtgagca cttgaaacag gcgactgtg   3120 gctgaggatt agaaattcca tttcgtgtca tttgaattgg cttaaatttt tttttttat    3180 tttattttt tgagacggag tcgcgctctg ttgcccaagc tggagtgcag tggcgcagtc    3240
tcagctcaat gcaacttccg tttcccaggt tcaagcaatt cttctacctc agcctcctga   3300
gtagctggga ctacaggcgc atgccaccac accccgctaa ttttttttgt attttagta    3360 gagatggggt ttcaccatgt tggccaggct ggtctcgaac tcctgacctt gtgatccacc   3420
cgcctcggcc tcccaaagtg ttgggattac aggcgtgagc caccgcgccc ggcagaactg   3480
acttaaattt aaacagccac atgtagttag tggccaccaa atgggacagc acacatctgg   3540
acacttccag gcttgttttg aagtcaggtg ggttcagagt ttcgcccagg gtttgacaca   3600
agatcggaga cagttttatg atgtacagat ggagagagag gcagagagag agagatccac   3660
agaagtccat gaggcgtttt accaccctct cagctgaaaa taacagaagt ctacatagaa   3720
gatgtgactt catagaacat atattgagca ccactgtcta ccagcacgtg tatgtgattg   3780
atgacccccc tcgtccactc acctccgcca ccaacaccag ataagtctga tgcatccagt   3840
gctcattggg tacactcatc aagatttttt tttttgtttt ttgcctgtaa tcccagctac   3900
tcgggaggct gaggcagaat tgcttgaacc tgagcggcag aggttgcagt gagccaagat   3960
cacgccactg cactccagcc tgggtgacag agcaagactt tgtcttggaa aaaaaaaaa    4020 agattttttt ttgttttttgt tgttttgttt gattttgggg tatttttag atggagtttc    4080 actctgtcac ccaggctgga gtgcactggt gcaatcttgg ttcactgcaa cctctacctc   4140
ccaggttcaa gcgattctca tgcctcagcc tcccgagtag ctgggactag aacaggcatg   4200
agccaccatg gccggctaat ttttatattt ttagtagaca gggtttcatc atgctggcca   4260
agctggtctt gctcctgacc tcacgtgatc cacccacctc ggcctcccaa agtgctggga   4320
ttacaggcgt gagccaccgc acccagccga ttttgggt ttttgagac agggtcccac      4380 tctgtcacct agactggagt acagtgatgg gatcatagct cactgcagcc ttgaattctc   4440
caggctcaag tgctcctcct gccccagctt ctcaagtagc tgggactata ggcacaagcc   4500
acaacaccta gctaattaaa aaaaatgtt tttgtagaga tggagtctca ctcactatat     4560
tgcccaggct ggtcttcaac tcctggtctc actcgattct cctgcctcag cctcccaaaa   4620
tgatgggatt acaggcgtga gccactgcac ctggcctcaa gtattttgta tacagtatag   4680
gttggatcca cacaacagct tatttggtta tttttccctg tctatctggt ttgaatccca   4740
gctccaccac ttttttggttc tgtgacattt cctgagttaa tttacctctc tgcacttgtt   4800
gaattccttg tttgtaaagt ggagatgata attatgctca ctatggattg ttttgaagat   4860
ttagtgagtc agacatttgg gatggtttct gacacatagc aagagccaaa atattatttt   4920
ttattcttgt taaaattatt attatgacca atgaggaaac gagtgaatag tgagaaggag   4980
atctttcctc tgcatcactc gggggttttt tgtttttgt ttttttttgc tgttgagaca    5040
gggtctcact ctgttgccca ggctggagtg caatagtgct atcactgctc actgcagtct   5100
```

```
tgacctccgg ggctcaagtg attcactgct ggcagttgat cttcttaaaa gtaacatgca      5160
ggccaggcac agtggctcac gcctgtaatc ccaacacttt gggagaccga ggcgggtgga      5220
tcacctgagg ttgggagttc gagaccagcc tgaccaacat ggagaagcca cgtgtctact      5280
aagaatacaa aattagctgg gcgtggtggc acacgcctgt aatcccagct actcaggagg      5340
ctgaggcagg agaatcactt gaacccagga ggcggaggtt gcagtgagcc aagattgcgc      5400
cattgcactc cagcctgggc agcaagaaca aaactctgtc tcaaaaaaaa aaaaaaaaa      5460 aaaaaaaaa aaaaaaaaa ggtaacatgc cttgaccagg catggtggct catgcctgta      5520
atcccagctc tttgggaggc tgaggcaagc ggatcacgag gtcaggagat ccaaaccatc      5580
ctggctaacg cggtgaaacc ccgtctctac taaaaataca aaaaattagc caggcacggt      5640
ggcacgcgcc tgtagtccca gctactcggg aggctgaggc aggagtatcg cttgaacccc      5700
ggaggcagag gttgcagtga gccgagatca ccactgca ctctagcctg gcgacagag      5760 tgagactcca tctcaaaaaa aaaaaaaaa aaaaagtaac atggatcaag atttggcaag      5820
aatgatttca tttagtcccc agggagggca catgcccca cttttcaagc ggtaaatctg      5880
aggctttgaa aaggggcagg cgtggtgagg ccacctagct gggtagggga tagaggcaag      5940
atttgaactc tgatgtatgt aaccacagcc tccgtgctgt ctccttttta acagcgacgt      6000
tcacttttga gaataagaac agcagcctct gtctgtggat ggtttgtgtg tcaggcagcc      6060
tgctgagaac cttcacacac agcatcttat ttagtgcggc aggaacccct tgagttaggg      6120
tcagcggaga tatttagaag cccagcacat gaaaaggat cctggaaact gccaacaccc      6180
tcctctaccc aaatatatat tcaaactaga accccacta acatagatga aaatccaaga      6240
atggcctaaa tgttcaccct gtgataatcc ttttaatgga ttcttagaat caagttattt      6300
aacaagcaga tattgtcccg ggggtagtgg gtggcagggg agaaggagaa gcttcactga      6360
tgacctgcat tcttgcttaa tggactctgg aaatttagca ttgcttcaaa atatagatta      6420
tttatttcca cttgacagag gaggatgctg aggctcaaaa ctgggaatga acttgcccca      6480
aatcacacag ctgagaagcg gcctagctct tacttacatt cagggctatg tagggacttc      6540
aataaaatcc ctaacaataa ccacagtaat agtattggga gcatctaacg tggtaggcac      6600
agctatgttt tgtacaccaa ttattttatt taggcctcct gggttcctat tataactgag      6660
aggtcatgtt ctccattcca cctggagctc agagaaggca taccatatgg acactgacag      6720
aagctgccag tgaaggagct ggggttcagg gtggcccaca agtcctcaaa taataacttg      6780
tgggagttgg ggggatggga actatgggag gttggaagct cctgcctcct tcatgttctg      6840
cccagatatc atttggtcag cgaggccccc ctgccactcc cctgcacac agttttgttg      6900 ttgttgttgt tgtttgagac agaatcttgc tctgtcatcc aggctggagt gcagtggcac      6960
aatcttggct cactgcaacc tcggcctcct ggattcaagc aattctcatg cctcagcctc      7020
ctgagtagct gggattacag gcatgcacca ccatgtccgg ctaattttg tatttttagt      7080 agagacagag ttttgccatg ttgcctagcc tggtccggaa ctcctgagct caaggcaatc      7140
cgcccacctc ggcctcccaa agtgctggga ttacaggcat gagccaccgc acccagccag      7200
gaccaccgta tttaaaattt caatcccca acttctggtg gtcccatcc ctgcctcatt      7260 ttttctccag agcaccatt accaaccatc aaactatatg ttttatttat ttaccatgtt      7320
tacattctgt atccctccat taggaagtaa actccatgtg acaaagaggt ttttttttt      7380 catttgttta atgctgggtc cccacaccaa gaacagtccc tggcacacag caggtgctca      7440
atgattattg gtacatagag tgaaagagat ggagcctcag gctgacctag agagcaaggc      7500
```

```
aggaggaaaa gataaaaggg cccctcccct ggggttttag gaccctccca acgcccccta    7560
agccagtctt ctctgccccc aggaccccg gaacaaacac aagttccgcc tgcatagcta     7620
cagcagcccc accttctgcg accactgtgg ctccctcctc tacgggcttg tgcaccaggg    7680
catgaaatgc tcctgtgagt gacctgggcc ttgccagggc ccttccaaag cgcccggtct    7740
gggttccggg aaatgcccgg gatggggtgg ggggtggagt cttggcttgg gggcggggcc    7800
tgaggtgcta cccgcagctt tcccctccag gctgcgagat gaacgtgcac cggcgctgtg    7860
tgcgtagcgt gccctccctg tgcggtgtgg accacaccga gcgccgcggg cgcctgcagc    7920
tggagatccg ggctcccaca gcagatgaga tccacgtaac tggtgaggcc ccgcccctc    7980 gcctggcccc gcccctccc caagtgtgag gcggggctga cccaaggcac ttgtgctggc     8040
ccagccctac cccaaagatg gggccacgcc tctttctatg gtcacgccca cactcctgac    8100
cccaccccaa aggccgagca cacccagcca tacccctttt ggctcgaagc cccgcctcca    8160
acctggcttc ttgcaacttt ctgcacctgt taatgacttt gactttcttt ttttttttgg    8220
gacggagttt cgctcttgtt gctcaagctg gagtgcaatg gcgcgatctc ggctcactgc    8280
aacttccgcc tccgggttc aagtgattct cctgcctcag cctcccgagt agctgggatt      8340
acaggcgcgt gtcaccaagc ccggctaatt ttttgtattt ttagtacaaa cggggtttca    8400
ccatgttagc caggctggtc tcgaactcct gaccccaggt gatccctcg actcggcctc     8460 ccaaagtgct gggattaaca ggcgtgagcc accgcgcctg gccaatggct ttcttttttg    8520
tttttatttt atgtttattt ttttgagatg gagtcttgct ctgtcaccca ggctggagtg    8580
cagtggtgca atcttggctc actgcaatct ctgcctccgg ggttcaaggg attctcctgc    8640
ctcagcctcc cgagtagctg gaattacagg cgcctgccac cacatccggc taattttttt    8700 ttttttttt ttttgagaca agatctcgct ctgttgccca ggctggagtg cagtagcatg     8760
atctcagctc actgcaacct ccgcctctca ggttcaagcg attctcctgc ttcagcctcc    8820
tgagtagctg ggactacagg tgcatgacac tgcacccagc tcattttgt atttttagta     8880 gagacagggt ttcaccatgc tagccaggct ggtctggaac tcctgacctc aggtgatccg    8940
cccgcctccg cctcccaaag tgctgggatt acagggtga ggaccgtgcc cggcaatggc      9000
tttctgggta taaggatctt gagaagggag agtacctggt tctgagggag gctgtggttc    9060
agtactggtg acatggccag ggtccaaact ctggttccta atggagagaa gggctctgga    9120
tctgatttca gggtcactgg ttgcggaaag ggctctatgc cctgtcttct gggttctgga    9180
gaggtaagaa gtcatgagaa acgagactga gagcttggaa ttcttttttt tttttttttg    9240
agacggagtc tcgctgtgac gcccaggctg gagtgcagtg gcgtaatctc ggctcactgc    9300
aagctccgac tcctgggttc acgtcattct cccgcctcag cctcctgagt agctgggacc    9360
acagacacct gccaccacgc ccagctaatt ttttttttt tttgtatttt tagtggagac     9420
ggggtttcac cattcacagg atggtctcga tctcctgacc ttgtgatccg cccgccttgg    9480
cctcccaaag tgctgggatt acaggcatga gccgccgtgc ctggccaagc ttggaactct    9540
tgattgctga ctggaggagg gctgggagcc ccttcctgga tctctaaccc gtcacactct    9600
tcctcactcc ccgtttagtt ggcgaggccc gtaacctaat tcctatggac cccaatggtc    9660
tctctgatcc ctatgtgaaa ctgaagctca tcccagaccc tcggaacctg acgaaacaga    9720
agacccgaac ggtgaaagcc acgctaaacc ctgtgtggaa tgagaccttt gtgttgtgag    9780
tctggggtgc agggaaggca atgacagctg acagagaatg atctgagggt cctagtggcc    9840
```

```
cccagagagc agctgatggg aggggttagg atagagggaa cccagaaaag ggcagaagaa      9900
gatggtggga aaagggaata gagtgattga gggagtggga tggagataca gaaacggaga      9960
gacagccaga ccactgtata attagtctcc attgaagccc ccaactttag agttagacag     10020
agatgagaga gagaagagag agtctcagaa gaggcagaaa cccaaagaga gacacagatg     10080
gagagggagg ggagaagatg ggggatggca gggagacaga gatcagttga caggaagaca     10140
gagtgataga gacccagaga ggagagaagg gtacagagac tcagagagag agatctcgag     10200
agacaagaga cagagatggg aaggggcgga gaatgcagga ggaagggaga ggaagagctc     10260
tctaggttta cttcaggccc caaagcccta gctggagaga gagcccggct gggaaggtca     10320
gaggtcggag accgacaaag caggagagga gccccagctg gctgggtttg cccccacctc     10380
cagcaccaag gatggggaac cgaggggagc catgagctcg gctctgcacc ccatccaccc     10440
caccttcctg cagcaacctg aagccagggg atgtggagcg ccggctcagc gtggaggtgt     10500
gggactggga ccggacctcc cgcaacgact tcatgggggc catgtccttt ggcgtctcgg     10560
agctgctcaa ggcgcccgtg gatggctggt gaggagcagg gctggggcct ggggatggag     10620
cgcaatatta ccatctccat ctgtgtgtgg tctctctcct ccaggccact gtccttccct     10680
ctgcctccca gcatgcgcac acacacacac acacacacac acacgcac acacgcac         10740
acacccctct ctctctattc ttctcttctt ctccctccc tttctccctc tccctctctt      10800
tttatctcac tcttctctc ttccatctct gtgtccgtct ctctgtgtct ctttcctccc     10860
ttccaatgtc tttgcctctc ccatgggtgc cccatccccg ctgcccgcct ctggtctccg     10920
tctgtatgtc aggtacaagt tactgaacca ggaggagggc gagtattaca atgtgccggt     10980
ggccgatgct gacaactgca gcctcctcca gaagtttgag gtacccagac cctggcttcc     11040
tcaagggagc ccagcccagc ctcccacggt tcagagctgg ccttttccttc caccctgag     11100
tgcccgctgg tcctgggact acagttccca gaagaccccta ggactccctc ctctgctctt     11160
ctaggggact cgagcccag ggtctgatgg gaattatagt tcctatctat cgccatggct      11220
tgagggtact aggggccacc agccctgtt ctagggcgat cccctgcatc tcttgggacc      11280
ctgactctct ctttcttttc tcccaggctt gtaactaccc cctggaattg tatgaggtga     11340
gtagaaccag ggcgttgaat ggaggcagtt tttgcctact tctctgattt cttattcctc     11400
ctctgacttc tgtcttcaat tccccacaca tgagttgagc acacatttgt gctaggcctg     11460
tcttgtgctt gctgaataat ccaggatcca gagatgaatc tgaccctcaa gcaactctcc     11520
aaggtaggga cacagtcaca gatacttaaa atacaggaag atgtgctaaa ttagaggtag     11580
cccagggcac tgaagaggcc taacggaggc actaatccag cctggggag ggtggtcagg      11640
gaggacttcc ctgaggaggt gacgcctgaa ttgattcttg aggtttttta aaatttttta     11700
atttatttt atttttattt ttatttttat ttctgtcgcc caggctggag tgcaatggca     11760
caatctcgcc tcactgcaac ctccagctcc cgggttcaag caattctctt gcctcagcct     11820
cctgagtagc tgggattaca ggtgaccgcc accacaccca gctaattttt tttttatttt     11880
tagtagagat gggatttcgc catgttggcc aggctgatct caaactccca aactcaggtg     11940
atccgcctgc cttggcctcc caaagtgctg ggattacagg catgagccac tgcgcccgac     12000
cgattcttga gttttttatt ttttttttga gacggagtct cgctgtgacg cccaggctgg     12060
agtgcagtgg tgcgatctcg gctcactgca agctccgcct cctgggttca cgccattctc     12120
ctgcatcagc ctcctgagta gctgggacta caggcgccca ccaccatgcc cggctaattt     12180
tttgtatttt tagtagagat gggtttcac cgtgttagcc aggatggtct cgatctcctg     12240
```

```
acctggtgat ccacccgcct cagcctccca aagtgctggg attacaggcg tgagccacca    12300
cacccagccg attcttgagt tttaaaaaat ctatcaagca tgatcatctt aatctctcca    12360
ttcattcatt cactcactga atatccttct ttttctttct ttctttcttt cttttttttt    12420
ttgagacaga atctcctttt gtcacccagg ttggagtgca gtgatgcagt ctcagctcac    12480
tgcaacctct gcctcccaga ttcaagtgat tctcctgcct cagcctcctg agtagttggg    12540
attacaggag cgcaccacca cacctggcta atttttgtat ttttagtaga gatgggtttc    12600 gacatgttg gccaggctgg tctcgaactc ctgacctcaa gtgatccacc cgccttggcc     12660
tcccaaagcg ctgagattag aggcgtgagc gaccacgccc agacgaatac ccattttcta    12720
gggtgtcata agccaggccc tgttctggga atagaatcag gccattccct ggtggagctc    12780
ttcttctagt ggaggacaaa gttacaaacc cagacattca caacgaggag caatgctgct    12840
gtaatggaga cagcctcagg cactggggcg tccctggcac agcctgagtc agagaaagct    12900
tcctagagag gtgagacctg gtagaagggc gggatttccc aaaggagaga ccagattttc    12960
aggcaggagg aagtaatgct ctctccctca tttaccctt caaaaaatac tttacagagc     13020
atctttgtgt gccaggcgtg gctctactca ctggggatat agagaaagca gggaaagaac    13080
aaacaaacaa acaaaaaagt cctttccctt atgggattta caccgggagg aagacattaa    13140
acaaaatata taagcatatg atagactggg cacgatgcct catgtctgtg atcctagtaa    13200
ggcgggcgga tcacctgagg tcaggagttt gagaccagcc tggccagcgt ggcaaaaccc    13260
catctctact aaaaaataca aaaatcagct gggcatggtg gaggcgcctg taatcccagc    13320
tactcggaag gctgaggcag gagaattgct ggattccggg aagtagaggc tgcagtgagc    13380
ccagatcgct ccactgcact ccagcctgga tgacagaggg agactctgtc tcaaaaaaaa    13440 aaaaaaaaa aagaagaca agaatcttca agattcaaca acagcaacaa catgttatag     13500
tctttactgg actcttacag aaactttcac cagagttttt aatgttgtgt gtggggttc     13560 acctgcatca gaattcctag agtgcttgct tttaaaagca cattcccag cctttctgca     13620 gacctactca gtgacgatct ctctgatgcc tcaaatgtct gcctactaaa ttaattcctc    13680
aggtgatcct tttgcaaagt taagtttgag aatgggctct gcggccgggc gcagtggctc    13740
acgcctgtca tcccagcact tgggaggcc aaggcgggtg gatcacgagg tcaggagatc     13800
gagaccatcc tggctaacac ggtgaatccc cgtctctact aaaaatacaa aaaattagc     13860 tgggcgtggt ggtgggtgcc tgtagtccca ggtactcagg aggctgaggc aggagaatgg    13920
catgaacctg ggaggtggag cttgcaatga gccgagatcg tgccactgca ctacagcctg    13980
ggtgacagag cgagactcta tctcagaaaa aaaaaaaaa gagagaatgg gctctgcagg     14040
agacaagggt accagcggga ggacattctg agccaaagag gtagagtctt ttgagatcag    14100
cagggatgat cctcccgtac aaacccaaga aacccagcag ggcagatggt gggcaaaggc    14160
ctagaggcag ggagtgtagg gtggtgtgtg tgcctgttgt ggctcacagc actctcccac    14220
agttcagcag gcaccactta atattaccaa tgaacaccaa ctctgtgcca agccttgagc    14280
taggtacggg gctaacaaca cagcaaacag aaacagccct gattattatt attattatta    14340
ttattattat tattattatt attattatgt atttatctat ttgagacaca gtctcgctct    14400
gtcgcccagg ctggaatgca gtggagcgat ctcagctcac tgcaacctct gcctcccggg    14460
ttcaagcgat tctcctgcct ggcctccca agtagctggg actacaggca gtgccacca     14520 tgtcctacta atttttatat tgctagtaga gatggggctt cgccatgttg gccaggctgg    14580
```

```
tcttgaactc ctgacctcag gtgatctgcc cacctcggcc tcccaaagtg ctgggattac    14640
aggcatgagc caccgcaccc agccctcaac aaatatttat gtagcctcaa tgaggtaggc    14700
agtgttactg tgtcttagcg aacaaagcag acccctgcct tagggagctc acaggcagaa    14760
agcagatagt cacacagata gatgtaaatt actaagaata aaagtgccag gaaggtgctg    14820
tccatggtga ccaaggggtg gtaagagagg catctgaccc agtttaaaaa gtcaggcgag    14880
gcctctatga agtgatgctt gagtcaaggt ctaaagggtg tttgggagac aactaggagg    14940 gaagggagg ggagagcttt acaggaagac ctaacggcac atccagaggc cctgaggtgg     15000
gagggaggac aatgagtgtc aggccagggt ggctggacca tggagcctgg gagagagaag    15060
aacaacctgc agtgtcagtc tcagcctggc tctgcaagtc atgtggaata aaatcttaac    15120
acagagggag cagttaaagg gtttacaagc atagggagga catgacctgg tttatttatt    15180
tttaaattgg ctcctgtgcc tgctgagtag agaatgcatt agaaagggca gccgtccatg    15240
tagagggaca agtgtggaag ctgtgacagc agcttagtct tgggcccct ccctgggggg     15300 ccgaggcagg aaaaggtaga gaagggaccc tagctgaaag ccaggtgtgc tccctggact    15360
ggcagcaccc atgtcaccca gaagcttttt acacataacg attctcaggt cccaccccag    15420
atttatagag ttagaaaatc tggcagtggg acccagcaat ctgttttacc aaaccctcta    15480
gggaattccg gcttagaggc taagagcaac cagattctag agctggactg cttgggtttc    15540
atttctggct ctgtccttta cctgctgtgt gacttggggc aagttactta acgtctctgt    15600
gctagtctcc tcttctgtaa aatggaaacg atagcagggt tttctggaaa cagcatatga    15660
taagctatct aaaaaaaaaa aagaagaaaa aaagagctaa gtgtttgttg aataataaat    15720
aaaccctcca ggctatgggg agtcagagaa aattaagcca aggacagggt aggagggtgg    15780 ccatttttcct ctgtctagcg attctcatcc tttcctttct tgggtgctgt gtctcttggg    15840
agcatttcct tatcgctgtg taaggtctaa ctgcctctgg ctctttcttt ctccttttcca   15900 cagcgggtgc ggatgggccc ctcttcctct cccatcccct cccccttcccc tagtcccacc   15960 gaccccaagc gctgcttctt cggggcgagt ccaggacgcc tgcacatctc cgacttcagc    16020
ttcctcatgt ttctaggaaa aggcagtttt gggaaggttg gattcctggg gttctggggg    16080
aaagggagga tgtctgtggg aaggtcagat ttctggttct tagggaggaa gtgggggtgg    16140
gaagagactg ggctcctgca tcttcaaata tggttaggtt gggccgttca ggttcctgga    16200
gaggagaggt ttacagatgt ggacactctc cttgagggga cgggcggcaa gtcagggctg    16260 tcagtcccctt aagagatgga ggaagggcct gggatcccgt ttccctgcgt cccttaggga   16320
gggggcaggt cctgtaccac tgggttccca acatggactg gccctttttgg aactgtgcgc   16380 ataggtgatg ctggccgagc gcaggggctc tgatgagctc tacgccatca agatcttgaa    16440
aaaggacgtg atcgtccagg acgacgatgt ggactgcacg ctggtggaga aacgtgtgct    16500
ggcgctgggg ggccggggtc ctggcggccg gccccacttc ctcacccagc tccactccac    16560
cttccagacc ccggtaagga tggaggggc ggaggctgtc ctccgggccc tgccttatcc     16620
agttctggac atctgcgttg ggattctgag tttagggcga ggcaagagaa ctttgtgctc    16680
tctgagtggg cgaggccagg cggattgtct cctcaggggg cgtggccggg gggggtcct    16740 tgggggggcgt ggccaggcga agggactcat cgggggggcgt ggccaggcgg aggggctcaa   16800
cggaggcgag gccgggtgga ggggctcctc ggggggcgtgg ccaggtggag ggactcatcg    16860
ggggcgtggg caggcagagg ggctcttcgc ggggcgtggt caggcggatg aaatctttgg    16920
gggggtggtt tagagggggcg ggctttgtca ggcgatggga tcattaatag gcgtggccag   16980
```

```
gcagattggc tccttggggg cgaggccagg cagacgagat tatgaatgag cgtatccagg    17040
caggtagatt cttcggaggg cgtggtcggg cggatgagct cctcggggc gtggccaggc     17100 ggtgagttcc tcggtggcat ggcctggcca ggtgaatggg tcctgcggag gtgtcgtgaa    17160
gcggttgagt tccttggggg cgtggccagg tggatgggct cttggggga gtggccagat     17220 gcctgtttcc ctggggagct tggtcttgag tggctgtagc cagtgctctg gaattttcag    17280
caaaggggca cagtggagga gggtgccttc ctagtgggcc tgcccagaat tgggctccga    17340
gtgacggggt catcactttt ggattctgac tgaaggacac atcagaaaca ggacattatt    17400
tccttaggat tgcgacttag gggcagagag tcagaacctg caagatttta agagggcgtg    17460
actttacttc caggggctcc gaatgagagt ggccagccac ctggattaaa atatatgtat    17520
gagcaacttt gattccttt ttttttttg agaaggagtt agctcttgtc ccccaggctg      17580
gagtgcaatg gcgcgatctc ggctcactgc aacctccgcc tcccgggttt aagcaattct    17640
cccgtctcag cctcctgagt agctgggatt acaggctccc gccaccacac tcagctgatt    17700
tttgtatttt tagtagagac cgggtttcgc cacgttggcc aggctggtct ggaactcctg    17760
acctcaggtg atccacccgc ttcggcctcc caaagtgctg ggattacagg cgtgagccac    17820
cacgcccagc tgcaactttg attcttagta ggaagccaga attgcatctg tgtgtgagtg    17880
gctgtgaaaa gagattttgg tgttcccgga tttcgagcga atggtgggct tcagtcttca    17940
attctgagaa ggcggggcca gaacacgtgg tctgatagtt ggcggtggtc tggcgggtgg    18000
agattctgag gtagcaggat tagcaccta gggccctccc agggatgtgg ctaggtgctc     18060
tgaatttctg gttgggtgca tctggaacct tccacgtctg tcctgagtga tcaggaaaga    18120
aattctccta ctctgggtag atggatcccg cctctaagcc catgcacttc tccgcaggac    18180
cgcctgtatt tcgtgatgga gtacgtcacc ggggagact tgatgtacca cattcaacag     18240
ctgggcaagt ttaaggagcc ccatgcagcg tgagtctcgg ccaacagaga atggtcgggg    18300
tggtggaagg gggcaggatc cagccactga ccttctgacg tccccaccca cccgtcctc    18360 caggttctac gcggcagaaa tcgctatcgg cctcttcttc cttcacaatc agggcatcat    18420
ctacaggtga gcagccccag gaatttccgt ggaggaaatc acgcccctgg aagggaaggg    18480
atttgaatat gtggctctag actgctgaac tcaacacttc ttgcaattcc tgccccacac    18540
ccctgcatcg tccagggacc tgaagctgga caatgtgatg ctggatgctg agggacacat    18600
caagatcact gactttggca tgtgtaagga aacgtcttc cccgggacga caacccgcac     18660
cttctgcggg accccggact acatagcccc ggaggtaacc ccaaccctgc tgctctggtc    18720
acgctttgag atcccttaga gggtgtagct gatggtccag tattccacac gggtgaggcc    18780
tgaccctcag accttgtcat gagttgtggc cttcttacac agccagtcgt tcctccagcc    18840
tccagcacag gtgagcttgg cactgagcct gccaggtggg cccagctggg tctctaaata    18900
ggtaaggtgg gcagcacctg tgggtgaatg ttccaggaga gtgggaccag ctcgtaggaa    18960
ttccaagtag gacctgaccc tggatccttc tgagaagggg cagacgattt ctagtgtact    19020
ctgagtgggt gtggcctgtc ccctgccaac actgaacatg tccggactat cttctgaata    19080
ctttaaactg gcagggctc tccctggagt attcagttgg atggaagctt atttcctgtg     19140
ttgtacgtgt ttctctgatg taagtgtact ggacttctgt gctgcatttt tcaagagggc    19200
aggatcagct gggcgcggtg gctcacacct gtaatcccag cactttggga ggctgaggca    19260
ggtggatcac ttgaggtcag gagtttgaga ccagcctggc caacatggtg aaacctcatc    19320
```

```
tctaacaaaa ttacacaaat tagccgggcg tggtggcatg cgcctgtaat cccagctatt    19380
cgggaggctg aggcaggaga atcgcttgaa ccggggaggc ggaggttgca gtgagctgag    19440
atcacaccac tgcactccag cctgggtgac agagcataac ttcataactt catctcaaaa    19500
aaaaaaaaaa aaaaaagccg ggtgcagtgg ctcacacctg taattccagc acttgggagg    19560
ctgaggcggg cggatcacaa ggtcaggagt ttgagaccag cctgactaac atggtgaaac    19620
tccatctcta ctaaaaatac aaaaattagc caggcgtggt ggcgggtgcc tgtagtccca    19680
gctacttggg aggctgaggc aggagaatta cttgaacccg ggaggtggag gttgcagtga    19740
gctgagatcg cgccactgca ctccagtctg ggcaacagag tgagaccctg tctcaaaaaa    19800
aaaaaaaaaa agaaaaagaa aaagggcagg gtgagatccc taaggttctg ggagagcaga    19860
tgctgtccta tgagtatttt aagtgggtgg ggtattaccc gactttgtta aaggggtggg    19920
gctgatgttc tgaatgtacg tatagatgga taaagcacat gcctgtagtc ccagctactt    19980
gggaggatgt gcctgactcg tgcccaaata atcaatgtca gtgatcacaa aacctggctg    20040
gtaatcagaa tcatctgtag aaaatttgaa aactgaggcc agacatggtg ctcatgcct    20100 gtaatcccag cactttggga agctgaggca ggcagatcac ttgaggtcag gaattcaaga    20160
ccagcctagc caacatggtg aaaccccgtc tctactaaaa atacaaaaat tagctggaca    20220
tggtgatgtg tgcctgtcaa cccagctact caggaggctg aggcaggaga atcacttgaa    20280
cccaggaggt ggaggttgca gtgagccaag attgcaccac tgcactgcat cctgggctac    20340
agagtgagac tccatctcaa aaagaaaaa agataagaaa atttgaaaac tacacacata    20400
ttcctgactc tgacacaaat attctaggtg ggtggaacca gtgacttggc cgttaggtag    20460
tctttctatt tgaggccaaa tgaatgtttg aagtaggtat gctttgtttc cagaatattc    20520
caaaagttag atcgctggcc aaaatattca gagtggaggc tgggcgtggt ggctcactcc    20580
tataatccca gcactttggg aggcggaggc aggccaattg cttgagtccg ggagtttgag    20640
accagcctgg gcaacatagt gaggacctat cttcactaaa agtgcaaaaa ttagccaggt    20700
gtggtggtgc acacctgtag cccacctact tgggaggctg aggtagaaga attacctgag    20760
cctgggaagt tgaggctgag tgagccgtga tcacactact gtgctccagc ctgggcaaca    20820
gagtgagacc ctgtcaaaaa aaaaaaaaaa aaaaaaaaa acgaaacaaa aaatcacctg    20880
atgaaataaa tattcagagt gggaagagct tgtgctgaaa gcacttaacg tgggtagcgc    20940
tcccaggggg tgaggccaga ggggtcctag gcttcctaaa gaacgcatca tgattcctg    21000 ccttccacct cccctagatc attgcctacc agcctatgg gaagtctgtc gattggtggt    21060
cctttggagt tctgctgtat gagatgttgg caggacaggt aagggaaggt ggggagaagc    21120
tggcttggct aaaagagaca gagaggggca cctggatctc aggaggagcc agttagaaag    21180
gagcccagaa ggttgtgctc gaatagcgct gtccatggtt ctgaagtgtt gtcttaatgt    21240
agaccaggtg ttttgttttg ttttgttttg tttgttctgt taccatggat tcttctcccc    21300
tagatggtaa agtagcagtc tggttaagcc tatggatccc ttctcagaag aatgttttc    21360 aatgcacaaa atagaataat acatacgcag aaaaccaagg ttcaaatcct cactttgcca    21420
cttactggct gtgtcagctt agacaattac atacattcta aatcagcttg attggattcc    21480
tggactgctg agtgtactac aactaaaaaa attggttacc acactcttga tcatcttctt    21540
agctggctat ggtagtgggc acctatagtc ccagctactg ggaggctga ggcaggaggg    21600 tcacatgagc ccaagaactc aaggttacac tgaactatga gtatgccact gtgttccagc    21660
acaggcgaca gagcaagacc ccatctcaaa agaacaaaca aacaaaagaa atcaatcatt    21720
```

```
ttgaaagata gtcaccaaaa cttttaaaat ttaattgaat ctaacaacca actaaattca   21780
atgtatacag ttgtctaaat atttaaaatt ggaaaatgga catatgtgca atttcttatt   21840
aattcattaa gtagtaagtt ctaatggtag taaagtaaaa aggagctcta acagtaattt   21900
tgatgtagca atgactaata atttggaata tctgcaactc tcatgtgatg agaaaatacc   21960
tgtgattact attgataatg aagccacaag cactgctgct gcctgcattc ataactgaag   22020
ggaatgctaa attttagtta gaagttaaaa aaaaatttgg ccggacatgg tggctcacgc   22080
ctgtaatcca agcactttgg gaggccgaag tgggcagatc acttgaggtc aggagtttga   22140
gaccagcctg gccaatatga tgaaacccca tctctaaatc tttgccttgg tatcattttt   22200
tgtaacctca gaagactgtg aactactcat ccaaccagga gaatgctttt agggtgtttc   22260
ctgcagtttt tcctctcttc tatttaactg acatgttgca taattaacag cctgctgatt   22320
tacatagcag ataagagag gcagaatagt acagagatgc acagatctga ggcatccgag   22380
ataggaaatg agagaacctg agaaggagag agatcaagct ttggtggttt ggtctgatct   22440
ctcctgaggg tgtggtcagg tgtgcatgtg gggcgtgtga tgggtcaggc atgttcccgg   22500
tggggtgagg agggtgtgga aggtttgggg aaaggcagtt gggcatgtcc ctgactctct   22560
atcccctcca ctttgatagc ctcccttcga tggggaggac gaggaggagc tgtttcaggc   22620
catcatggaa caaactgtca cctaccccaa gtcgctttcc cgggaagccg tggccatctg   22680
caagggggtg agagccccct gactcccagc ttctccaggc tcacaaccac acaccccatt   22740
gctgtctctg tgcctattag aaaaatgctc ccattcctga agtcacttta cttccatctg   22800
ttggaaaagt tgatatgatg cataggtttt gttagaacaa tgatttccag ccctgttgcc   22860
acgaggcctg gagatggcct ctgtctcatc cttctctgtg actcccactc cccagctccc   22920
tgcttgcagg aagtgctgaa agtccagggt gtctgtctgt ctagaactgg gtgggtcagg   22980
taaacccaac ttctgcagct tttcttcctg tgtgaacttg ggtgagtcac caaaactttg   23040
tgagcttaac tctcttcagg ggttatggag ttgacacaga agaaagcacc tggcccatag   23100
cagattttca gcccatgtca gcaccttctg cgtctagctg ctctctctgc atctccctga   23160
cagtctctct ggtttctgtc tcatgcctcc cctccatctg catacgatgg ggctctctgt   23220
gtttcttcct tttctctgtg tctccttctg catctctgtc tacacttttg ggcctttgtc   23280 caaccccct accccatc tctgtccct cctgtgtcca ctctcataca cacacgctac   23340
atctcaccct cctctcctgc tggctttctg tcctcccttt tctctgggtc tctgtcccca   23400
tatttggtct ttattcctcc ctctgggtgt gtgtttcctg ggtctctatc cttctctctt   23460
tctgaatctc tgtcccctg ggtctcctct gtctcctccc ttctctgagt ttctgccttc   23520
ttacctgggg tctctgtacc accctctgaa tttctatttc ccctttctc tgggtctgca   23580 acctctcttc ccccattccc tccctcttcc ccttcatctc ctctacccttt cctccctcc   23640 ccctaccgac ctccctctgt ccttcactct ccccttccct ccctcccct acccttccct   23700 ctccccgtcc ctctctcccc ttccctctct ccccctaccc cttttccctc tcctcttctc   23760
catctccctc atgatttgtt ctgtttctct gtgtgtccct gggtctctgg gtatgaattt   23820
catctgctat cattttcatg tatcctctcc ttcttcctgt ctctctctct ctctctctca   23880
ctcactctca ccctctgtct ctctctctct ctgtccctct tcctctctct tcctctctg   23940 tctctctctg tctcgctctc tgtctgtctc cctcctcctc ctcctcccctc ctcctcctcc   24000 tcctcctcct cctcctcctc ctcctcctcc ttcttcttct tcttcttctt cttcttcttc   24060
```

```
ttcttttctt ctctctctct ctcctttctt ttcccttcct ccctccattt gcctgtttcc    24120
cctggctgtt cttatctctc cggatctcat gcctgtgtct cttggttcct ccatctgcct    24180
gtctctgtcc ctctttctct gggtctacct gtccggcact ctgtctgttt gtctgtctgt    24240
ctctctctgt gtttcccaca gttcctgacc aagcacccag ggaagcgcct gggctcaggg    24300
cctgatgggg aacctaccat ccgtgcacat ggcttttcc gctggattga ctgggagcgg     24360
ctggaacgat tggagatccc gcctcctttc agaccccgcc cggtcagtca ccctccaggc    24420
aacaaaaacc tggtccctga aggggtgggg ttcccctggg cctcaatata cctgtatgtg    24480
ggggtggggt tccctctgca gagcccccg cccccaacaa aaggaggtgc agacaccatg     24540
aagcatgaat agagattctg caggagacag gagatgagac tggggtacac agagggacac    24600
ccgaggagcc ctcggagctg cttaactttc cctcccccac gtctcccaca gtgtggccgc    24660
agcggcgaga actttgacaa gttcttcacg cgggcggcgc cagcgctgac ccctccagac    24720
cgcctagtcc tggccagcat cgaccaggcc gatttccagg gcttcaccta cgtgaaccc     24780
gacttcgtgc accggatgc ccgcagcccc accagcccag tgcctgtgcc cgtcatgtaa     24840
tctcacccgc cgccactagg tgtccccaac gtcccctccg ccgtgccggc ggcagcccca    24900
cttcaccccc aacttcacca cccccctgtcc cattctagat cctgcacccc agcattccag   24960
ctctgccccc gcgggttcta gacgcccctc ccaagcgttc ctggccttct gaactccata    25020
cagcctctac agccgtcccg cgttcaagac ttgagcggag cccgatattc tccctgacct    25080
tagcgttctg gactctgccc caatcgggtc cagagaccac accactaacc atccccaact    25140
ccatggggtt cgagactcca tcttggtagt tctgtgcctc ccccagacc ccgcccctgg     25200
ggaaatagcc tcacggggtt ggctgttcca gactcaggtt ccagaacagc cctcggcctc    25260
cgaggctccc cgcctccact ctagttctag atgagtggga g                       25301
```

<210> SEQ ID NO 4
<211> LENGTH: 18
<212> TYPE: DNA
<213> ORGANISM: Homo Sapien

<400> SEQUENCE: 4
ctgcctttgg ctcttcct    18

<210> SEQ ID NO 5
<211> LENGTH: 20
<212> TYPE: DNA
<213> ORGANISM: Homo Sapien

<400> SEQUENCE: 5
taggagtctg caccctagt    20

<210> SEQ ID NO 6
<211> LENGTH: 20
<212> TYPE: DNA
<213> ORGANISM: Homo Sapien

<400> SEQUENCE: 6
ctggattcct gggtctgaag    20

<210> SEQ ID NO 7
<211> LENGTH: 18
<212> TYPE: DNA
<213> ORGANISM: Homo Sapien

<400> SEQUENCE: 7

```
cagcctccac cctcctga                                                 18

<210> SEQ ID NO 8
<211> LENGTH: 20
<212> TYPE: DNA
<213> ORGANISM: Homo Sapien

<400> SEQUENCE: 8
cgctctctct ttccaatttt                                               20

<210> SEQ ID NO 9
<211> LENGTH: 19
<212> TYPE: DNA
<213> ORGANISM: Homo Sapien

<400> SEQUENCE: 9
gaggaggaga accaggtgt                                                19

<210> SEQ ID NO 10
<211> LENGTH: 20
<212> TYPE: DNA
<213> ORGANISM: Homo Sapien

<400> SEQUENCE: 10
caaggcagga ggaaaagata                                               20

<210> SEQ ID NO 11
<211> LENGTH: 18
<212> TYPE: DNA
<213> ORGANISM: Homo Sapien

<400> SEQUENCE: 11
atttcccgga acccagac                                                 18

<210> SEQ ID NO 12
<211> LENGTH: 20
<212> TYPE: DNA
<213> ORGANISM: Homo Sapien

<400> SEQUENCE: 12
catgaaatgc tcctgtgagt                                               20

<210> SEQ ID NO 13
<211> LENGTH: 18
<212> TYPE: DNA
<213> ORGANISM: Homo Sapien

<400> SEQUENCE: 13
acaagtgcct tgggtcag                                                 18

<210> SEQ ID NO 14
<211> LENGTH: 20
<212> TYPE: DNA
<213> ORGANISM: Homo Sapien

<400> SEQUENCE: 14
gcttggaact cttgattgct                                               20

<210> SEQ ID NO 15
<211> LENGTH: 20
<212> TYPE: DNA
<213> ORGANISM: Homo Sapien
```

<400> SEQUENCE: 15
ccactaggac cctcagatca                                              20

<210> SEQ ID NO 16
<211> LENGTH: 18
<212> TYPE: DNA
<213> ORGANISM: Homo Sapien

<400> SEQUENCE: 16
acctccagca ccaaggat                                                18

<210> SEQ ID NO 17
<211> LENGTH: 20
<212> TYPE: DNA
<213> ORGANISM: Homo Sapien

<400> SEQUENCE: 17
cacacacaga tggagatggt                                              20

<210> SEQ ID NO 18
<211> LENGTH: 20
<212> TYPE: DNA
<213> ORGANISM: Homo Sapien

<400> SEQUENCE: 18
cttccaatgt ctttgcctct                                              20

<210> SEQ ID NO 19
<211> LENGTH: 20
<212> TYPE: DNA
<213> ORGANISM: Homo Sapien

<400> SEQUENCE: 19
atgtgtgggg aattgaagac                                              20

<210> SEQ ID NO 20
<211> LENGTH: 20
<212> TYPE: DNA
<213> ORGANISM: Homo Sapien

<400> SEQUENCE: 20
ttgggagcat ttccttatcg                                              20

<210> SEQ ID NO 21
<211> LENGTH: 20
<212> TYPE: DNA
<213> ORGANISM: Homo Sapien

<400> SEQUENCE: 21
aaatctgacc ttcccacaga                                              20

<210> SEQ ID NO 22
<211> LENGTH: 20
<212> TYPE: DNA
<213> ORGANISM: Homo Sapien

<400> SEQUENCE: 22
tcccttaaga gatggaggaa                                              20

<210> SEQ ID NO 23
<211> LENGTH: 20
<212> TYPE: DNA
<213> ORGANISM: Homo Sapien

```
<400> SEQUENCE: 23
ctcgccctaa actcagaatc                                                20

<210> SEQ ID NO 24
<211> LENGTH: 20
<212> TYPE: DNA
<213> ORGANISM: Homo Sapien

<400> SEQUENCE: 24
gtctgatagt tggcggtggt                                                20

<210> SEQ ID NO 25
<211> LENGTH: 19
<212> TYPE: DNA
<213> ORGANISM: Homo Sapien

<400> SEQUENCE: 25
agaaggtcag tggctggat                                                 19

<210> SEQ ID NO 26
<211> LENGTH: 19
<212> TYPE: DNA
<213> ORGANISM: Homo Sapien

<400> SEQUENCE: 26
atccagccac tgaccttct                                                 19

<210> SEQ ID NO 27
<211> LENGTH: 18
<212> TYPE: DNA
<213> ORGANISM: Homo Sapien

<400> SEQUENCE: 27
cagtgccaag ctcacctg                                                  18

<210> SEQ ID NO 28
<211> LENGTH: 20
<212> TYPE: DNA
<213> ORGANISM: Homo Sapien

<400> SEQUENCE: 28
gggaagagct tgtgctgaaa                                                20

<210> SEQ ID NO 29
<211> LENGTH: 20
<212> TYPE: DNA
<213> ORGANISM: Homo Sapien

<400> SEQUENCE: 29
ctaactggct cctcctgaga                                                20

<210> SEQ ID NO 30
<211> LENGTH: 20
<212> TYPE: DNA
<213> ORGANISM: Homo Sapien

<400> SEQUENCE: 30
ggcatccgag ataggaaatg                                                20

<210> SEQ ID NO 31
<211> LENGTH: 20
<212> TYPE: DNA
```

```
<213> ORGANISM: Homo Sapien

<400> SEQUENCE: 31
tcaggaatgg gagcattttt                                                    20

<210> SEQ ID NO 32
<211> LENGTH: 20
<212> TYPE: DNA
<213> ORGANISM: Homo Sapien

<400> SEQUENCE: 32
ttctctgggt ctacctgtcc                                                    20

<210> SEQ ID NO 33
<211> LENGTH: 20
<212> TYPE: DNA
<213> ORGANISM: Homo Sapien

<400> SEQUENCE: 33
gtgtctgcac ctccttttgt                                                    20

<210> SEQ ID NO 34
<211> LENGTH: 22
<212> TYPE: DNA
<213> ORGANISM: Homo Sapien

<400> SEQUENCE: 34
cagacaccat gaagcatgaa ta                                                 22

<210> SEQ ID NO 35
<211> LENGTH: 20
<212> TYPE: DNA
<213> ORGANISM: Homo Sapien

<400> SEQUENCE: 35
ttagtggtgt ggtctctgga                                                    20
```